US008796376B2

(12) United States Patent
Kulkarni et al.

(10) Patent No.: US 8,796,376 B2
(45) Date of Patent: Aug. 5, 2014

(54) FUNCTIONALIZED POLYMERS AND OLIGOMERS

(75) Inventors: Rahul R. Kulkarni, Houston, TX (US); Pradeep P. Shirodkar, Houston, TX (US); Alistair D. Westwood, Kingwood, TX (US); Donna J. Crowther, Seabrook, TX (US); Wei Tang, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 149 days.

(21) Appl. No.: 13/430,247

(22) Filed: Mar. 26, 2012

(65) Prior Publication Data

US 2013/0253120 A1    Sep. 26, 2013

(51) Int. Cl.
| | |
|---|---|
| *C09D 5/16* | (2006.01) |
| *C09D 123/36* | (2006.01) |
| *C08K 3/34* | (2006.01) |
| *C07D 237/08* | (2006.01) |
| *C08F 8/30* | (2006.01) |
| *C08L 23/36* | (2006.01) |

(52) U.S. Cl.
USPC ........ 524/447; 524/445; 524/570; 525/333.2; 525/333.7; 525/333.9; 525/334.1; 525/375; 525/376

(58) Field of Classification Search
CPC .................................. C08F 8/30; C08F 26/06
USPC ............ 524/447, 445, 570; 525/333.7, 333.9, 525/334.1, 375, 376; 544/224; 977/773; 526/258
See application file for complete search history.

(56) References Cited

U.S. PATENT DOCUMENTS

| | | | |
|---|---|---|---|
| 3,022,305 | A | 2/1962 | Carboni |
| 3,235,484 | A | 2/1966 | Colfer |
| 4,069,023 | A | 1/1978 | Brois et al. |
| 4,110,377 | A | 8/1978 | Clerici et al. |
| 4,197,398 | A | 4/1980 | Floyd et al. |
| 4,619,756 | A | 10/1986 | Dickakian |
| 4,973,414 | A | 11/1990 | Nerger et al. |
| 5,026,948 | A | 6/1991 | Forbus |
| 5,211,834 | A | 5/1993 | Forester |
| 5,229,022 | A | 7/1993 | Song et al. |
| 5,252,677 | A | 10/1993 | Tomita et al. |
| 5,266,186 | A | 11/1993 | Kaplan |
| 5,382,634 | A | 1/1995 | Koyama et al. |
| 5,439,607 | A | 8/1995 | Patil |
| 5,741,946 | A | 4/1998 | Wei |
| 5,744,541 | A | 4/1998 | Sawaguchi et al. |
| 5,750,815 | A | 5/1998 | Grubbs et al. |

(Continued)

FOREIGN PATENT DOCUMENTS

| | | |
|---|---|---|
| CN | 101011062 | 8/2007 |
| DE | 2041797 | 3/1972 |

(Continued)

OTHER PUBLICATIONS

Rustemeyer et al. J. Mater. Chem., 1999, 9, 2245-2250.*

(Continued)

*Primary Examiner* — Vu A Nguyen
(74) *Attorney, Agent, or Firm* — Catherine L. Bell

(57) ABSTRACT

A functionalized polyolefin having one or more pyridazine moieties is disclosed herein. A method to produce the functionalized polyolefin is also disclosed. A composition including the functionalized polyolefin is also disclosed.

22 Claims, 6 Drawing Sheets

$^1$H NMR Vinyl Terminated Polypropylene $^1$H NMR Sample A

(56) References Cited

U.S. PATENT DOCUMENTS

| | | |
|---|---|---|
| 5,756,428 A | 5/1998 | Emert et al. |
| 6,017,859 A | 1/2000 | Rossi et al. |
| 6,114,445 A | 9/2000 | Tzoganakis et al. |
| 6,117,962 A | 9/2000 | Weng et al. |
| 6,143,686 A | 11/2000 | Vizzini et al. |
| 6,197,910 B1 | 3/2001 | Weng et al. |
| 6,225,432 B1 | 5/2001 | Weng et al. |
| 6,268,518 B1 | 7/2001 | Resconi et al. |
| 6,326,427 B1 | 12/2001 | Birnbrich et al. |
| 6,359,091 B1 | 3/2002 | Godschalx et al. |
| 6,410,666 B1 | 6/2002 | Grubbs et al. |
| 6,444,773 B1 | 9/2002 | Markel |
| 6,448,350 B1 | 9/2002 | Dall'Occo et al. |
| 6,476,167 B2 | 11/2002 | Peters |
| 6,534,611 B1 | 3/2003 | Darling et al. |
| 6,646,081 B2 | 11/2003 | Godschalx et al. |
| 6,703,457 B2 | 3/2004 | Van Baar et al. |
| 6,750,307 B2 | 6/2004 | Weng et al. |
| 6,897,261 B1 | 5/2005 | Machida et al. |
| 6,939,930 B2 | 9/2005 | Reinking et al. |
| 7,126,031 B2 | 10/2006 | Boussie et al. |
| 7,247,385 B1 | 7/2007 | Tzoganakis et al. |
| 7,276,567 B2 | 10/2007 | Voskoboynikov et al. |
| 7,589,160 B2 | 9/2009 | Resconi et al. |
| 7,820,607 B2 | 10/2010 | Matsuda et al. |
| 7,943,716 B2 | 5/2011 | Resconi et al. |
| 7,960,487 B2 | 6/2011 | Yang et al. |
| 8,058,351 B2 | 11/2011 | Pawlow et al. |
| 2002/0137978 A1 | 9/2002 | Grubbs et al. |
| 2003/0161752 A1 | 8/2003 | Luk et al. |
| 2004/0127649 A1 | 7/2004 | Arjunan |
| 2004/0214953 A1 | 10/2004 | Yamada et al. |
| 2004/0249046 A1 | 12/2004 | Abhari et al. |
| 2005/0054793 A1 | 3/2005 | Reinking et al. |
| 2005/0159299 A1 | 7/2005 | Rodriguez et al. |
| 2005/0215693 A1 | 9/2005 | Wang et al. |
| 2005/0261440 A1 | 11/2005 | Dickakian et al. |
| 2006/0052553 A1 | 3/2006 | Resconi et al. |
| 2006/0083945 A1 | 4/2006 | Morishita et al. |
| 2006/0270814 A1 | 11/2006 | Mako et al. |
| 2006/0280982 A1 | 12/2006 | Kanaoka et al. |
| 2007/0293640 A1 | 12/2007 | Jiang et al. |
| 2008/0228017 A1 | 9/2008 | Burdett et al. |
| 2008/0234451 A1 | 9/2008 | Kenwright et al. |
| 2008/0251460 A1 | 10/2008 | Gstrein et al. |
| 2008/0293937 A1 | 11/2008 | Marks et al. |
| 2009/0149623 A1 | 6/2009 | Higami et al. |
| 2009/0205969 A1 | 8/2009 | Jimenez et al. |
| 2009/0221750 A1 | 9/2009 | Tsunogae et al. |
| 2009/0247441 A1 | 10/2009 | Baum |
| 2009/0264544 A1 | 10/2009 | Loy |
| 2009/0318640 A1 | 12/2009 | Brant et al. |
| 2009/0318644 A1 | 12/2009 | Brant et al. |
| 2009/0318646 A1 | 12/2009 | Brant et al. |
| 2009/0318647 A1 | 12/2009 | Hagadorn et al. |
| 2010/0069573 A1 | 3/2010 | Arriola et al. |
| 2010/0152387 A1 | 6/2010 | Steininger et al. |
| 2010/0152388 A1 | 6/2010 | Jiang et al. |
| 2010/0180947 A1 | 7/2010 | Smith et al. |
| 2011/0124820 A1 | 5/2011 | Lee et al. |

FOREIGN PATENT DOCUMENTS

| | | |
|---|---|---|
| EP | 0 767 182 | 4/1997 |
| EP | 0 802 216 | 10/1997 |
| EP | 0 958 309 | 11/1999 |
| EP | 1 361 232 | 11/2003 |
| EP | 1 849 757 | 10/2007 |
| EP | 1 862 491 | 12/2007 |
| EP | 1 906 473 | 4/2008 |
| EP | 2 154 173 | 2/2010 |
| FR | 2 437 243 | 4/1980 |
| FR | 2 910 004 | 6/2008 |
| GB | 1 310 847 | 3/1973 |
| JP | 47034499 | 11/1972 |
| JP | 02-064115 | 3/1990 |
| JP | 1993/320260 | 3/1993 |
| JP | 2000/038420 | 2/2000 |
| JP | 2005-093181 | 4/2005 |
| JP | 2005/139284 | 6/2005 |
| JP | 2005/336092 | 12/2005 |
| JP | 2006-342244 | 12/2006 |
| JP | 2007/169340 | 7/2007 |
| JP | 2007/246433 | 9/2007 |
| JP | 2008/050278 | 3/2008 |
| JP | 2008-287976 | 11/2008 |
| JP | 2008-291061 | 12/2008 |
| JP | 2010-013625 | 1/2010 |
| JP | 2010/037555 | 2/2010 |
| JP | 2011/026448 | 2/2011 |
| JP | 2012/051859 | 3/2012 |
| JP | 2012/052062 | 3/2012 |
| NL | 7010357 | 10/1970 |
| SU | 498300 | 1/1976 |
| WO | WO 95/27717 | 10/1995 |
| WO | WO 97/47665 | 12/1997 |
| WO | WO 98/16508 | 4/1998 |
| WO | WO 99/05182 | 2/1999 |
| WO | WO 99/28354 | 6/1999 |
| WO | WO 99/46270 | 9/1999 |
| WO | WO 00/00576 | 1/2000 |
| WO | WO 00/55218 | 9/2000 |
| WO | WO 02/079127 | 10/2002 |
| WO | WO 2004/031250 | 4/2004 |
| WO | WO 2004/076545 | 9/2004 |
| WO | WO 2005/092935 | 10/2005 |
| WO | WO 2006/069742 | 7/2006 |
| WO | WO 2006/127483 | 11/2006 |
| WO | WO 2007/003238 | 1/2007 |
| WO | WO 2007/045634 | 4/2007 |
| WO | WO 2008/027268 | 3/2008 |
| WO | WO 2008/087263 | 7/2008 |
| WO | WO 2008/141941 | 11/2008 |
| WO | WO 2009/009158 | 1/2009 |
| WO | WO 2009/042825 | 4/2009 |
| WO | WO 2009/053594 | 4/2009 |
| WO | WO 2009/134227 | 11/2009 |
| WO | WO 2009/155517 | 12/2009 |
| WO | WO 2010/057922 | 5/2010 |

OTHER PUBLICATIONS

Rodriguez et al. Proceedings of the ACS Division of Polymeric Materials: Science and Engineering, 1990, vol. 63, pp. 376-382.*

Becer et al., "*Click Chemistry Beyond Metal-Catalyzed Cycloaddition*", Angewandte Chemie, International Edition, 2009, vol. 48, No. 27, pp. 4900-4908.

Carboni et al., "*Reactions of Tetrazines with Unsaturated Compounds. A New Synthesis of Pyridazines*", Journal of the American Chemical Society, 1959, vol. 81, No. 16, pp. 4342-4346.

Clavier et al., "*s-Tetrazines as Building Blocks for New Functional Molecules and Molecular Materials*", Reviews, 2010, vol. 110, No. 6, pp. 3299-3314.

Ding et al., "*The Preparation of 3,6-Bis(3-hexylthien-2-yl)-s-tetrazine and Its Conjugated Polymers*", Journal of Polymer Science Part A: Polymer Chemistry, 2011, vol. 49, No. 15, pp. 3374-3386.

Hoogenboom et al., "*Synthesis of star-shaped poly(ϵ-caprolactone) via 'click' chemistry and 'supramolecular click' chemistry*", Chemical Communications, 2006, pp. 4010-4012.

Hoogenboom et al., "*Synthesis and Characterization of Novel Substituted 3,6-Di(2-pyridyl)pyridazine Metal Coordinating Ligands*", European Journal of Organic Chemistry, 2003, vol. 2003, No. 24, pp. 4887-4896.

Kovalev et al., "*Cycloaddition to sym-Tetrazines (The Corboni-Lindsey Reaction) (Review)*", Chemistry of Heterocyclic Compounds, 1981, vol. 17, No. 11, pp. 1063-1076.

Yanjarappa et al., "*Recent Developments in the Synthesis of Functional Poly(olefin)s*", Progress in Polymer Science, 2002, vol. 27, No. 7, pp. 1347-1398.

Amin et al., *Versatile Pathways for In Situ Polyolefin Functionalization with Heteroatoms: Catalytic Chain Transfer*, Angew. Chem. Int. Ed., 2008, vol. 47, No. 11, pp. 2006-2025.

(56) References Cited

OTHER PUBLICATIONS

Balboni et al., $C_2$-*Symmetric Zirconocenes for High Molecular Weight Amorphous Poly(propylene)*, Macromolecular Chemistry and Physics, 2001, vol. 202, No. 10, pp. 2010-2028.
Britovsek et al., *Novel Olefin Polymerization Catalysts Based on Iron and Cobalt*, Chemical Communications, 1998, No. 7, pp. 849-850.
Britovsek et al., *Iron and Cobalt Ethylene Polymerization Catalysts Bearing 2, 6-Bis(Imino)Pyridyl Ligands: Synthesis, Structures, and Polymerization Studies*, Journal of the American Chemical Society, 1999, vol. 121, No. 38, pp. 8728-8740.
Brzezinska et al., *Synthesis of ABA Triblock Copolymers via Acyclic Diene Metathesis Polymerization and Living Polymerization of α-Amino Acid-N-Carboxyanhydrides*, Macromolecules, 2001, vol. 34, pp. 4348-4354.
Bujadoux et al., *Use of bridged and non-bridged metallocene catalysts in high pressure/high temperature ethylene/α-olefin copolymerization*, Metallocene Polymers, 1995, pp. 377-402.
Chen et al., Reactive & Functional Polymers, 2008, vol. 68, No. 9, pp. 1307-1313.
Corey et al., *"Reactions of Hydrosilanes and Olefins in the Presence of $Cp_2MCl_2/nBuLi$"*, Organometallics, 1992, vol. 11, pp. 672-683.
Cossy et al., *"Cross-Metathesis reaction. Generation of Highly Functionalized Olefins from Unsaturated Alcohols"*, Journal of Organometallic Chemistry, 2001, vol. 634, Issue 2, pp. 216-221.
Hansell et al., *Additive-Free Clicking for Polymer Functionalization and Coupling by Tetrazine-Norbornene Chemistry*, Journal of the American Chemical Society, 2011, vol. 133, No. 35, pp. 13828-13831.
Herzon et al., *"Direct, Catalytic Hydroaminoalkylation of Unactivated Olefins with N-Alkyl Arylamines"*, JACS, 2007, vol. 129, pp. 6690-6691.
Herzon et al., *"Hydroaminoalkylation of Unactivated Olefins with Dialkylamines"*, JACS, 2007, vol. 130, pp. 14940-14941.
Kesti et al., *"Group 4 Metallocene Olefin Hydrosilyation Catalysts"*, Organometallics, 1992, vol. 11, pp. 1095-1103.
Kolodka et al., *"Copolymerization of Propylene with Poly(Ethylene-Co-Propylene) Macromonomer and Branch Chain-Length Dependence of Rheological Properties"*, Macromolecules, 2002, vol. 35, pp. 10062-10070.
Koo et al., *"Silicon-Modified Ziegler-Natta Polymerization. Catalytic Approaches to Silyl-Capped and Silyl-Linked Polyolefins Using "Single-Site" Cationic Ziegler-Natta Catalysts"*, Journal of American Chemical Society, 1999, vol. 121, pp. 8791-8802.
Liu et al., *Kinetics of Initiation, Propagation, and Termination for the [rac-(C2H4(1-indenyl)2)ZrMe] {MeB(C6F5)3]-Catalyzed Polymerization of 1-Hexene*, Journal of the American Chemical Society, 2001, vol. 123, pp. 11193-11207.
Markel, et al., *"Metallocene-Based Branch-Block Thermoplastic Elastomers"*, Macromolecules, 2000, vol. 33, pp. 8541-8548.
Mathers et al., *Cross Metathesis Functionalization of Polyolefins*, Chemical Communications—Chemcom, Royal Society of Chemistry, 2004, No. 4, pp. 422-423.
Nagai et al., *Novel Well-defined Funcationalized Polyolefins and Polyolefin-polar Polymer Block Copolymers: Formations and Their Features*, Poly Preprints, 2008, vol. 49, No. 2, 776-777.
Nakatsuka et al., *Creation and Application of New Materials by a Fusion of FI-catalyst Technology and Fine Organic Synthesis Technology*, Shokubai, 2010, vol. 52, No. 8, pp. 569-574.
Ornelas et al., *Cross Olefin Metathesis for the Selective Functionalization, Ferrocenylation, and Solubilization in Water of Olefin-Terminated Dendrimers, Polymers, and Gold Nanoparticles and for a Divergent Dendrimer Constructions*, Journal of American Chemical Soc., 2008, vol. 130, No. 4, pp. 1495-1506.
Passaglia et al., *"Grafting of Diethyl Maleate and Maleic Anhydride Onto Styrene-b-(Ethylene-co-1-Butene)-b-Styrene Triblock Copolymer (SEBS)"*, Polymer, 2000, vol. 41, pp. 4389-4400.
Quirk et al., *"Anionic Synthesis of Secondary Amine Functionalized Polymers by Reaction of Polymeric Organolithiums with N-Benzylidenemethylamine"*, Macromolecular Chemistry and Physics, 2002, vol. 203, pp. 1178-1187.
Resconi et al., *Chain Transfer Reactions in Propylene Polymerization with Zirconocene Catalysts*, Topics in Catalysis, 1999, vol. 7, No. 1-4, pp. 145-163.
Rodriguez et al., *Poly(4-vinylpyridazine). First Synthesis, Characterization and Properties*, Polymeric Materials Science and Engineering, Proceedings of the ACS Division of Polymeric Materials Science and Engineering, 1990, vol. 63, pp. 376-382 (Abstract).
Rose et al., *"Poly(ethylene-co-propylene macromonomer)s: Synthesis and Evidence for Starlike Conformaitons in Dilute Solution"*, Macromolecules, 2008, vol. 41, pp. 559-567.
Rybak et al., *"Acyclic Diene Metathesis with a Monomer with a Monomer from Renewable Resources: Control of Molecular Weight and One-Step Preparation of Block Copolymers"*, ChemSusChem, 2008, vol. 1, pp. 542-547.
Shiono et al., *Copolymerization of poly(propylene) macromonomer with ethylene by (tert-butanamide)dimethyl(tetramethyl-qscyclopentadienyl) silane titanium dichloride/methylaluminoxane catalyst*, Macromol. Chem. Phys., 1997, vol. 198, pp. 3229-3237.
Weng et al., *Synthesis of Long-Chain Branched Propylene Polymers via Macromonomer Incorporation*, Macromol. Rapid Commun., 2001, vol. 22, No. 18, pp. 1488-1492.
Weng et al., *Synthesis of Vinyl-Terminated Isotactic Poly(propylene)*, Macromol. Rapid Commun., 2000, 21, No. 16, pp. 1103-1107.
Weng et al., Long Chain Branched Isotactic Polypropylene, Macromolecules, 2002, vol. 35, pp. 3838-3843.
Wu et al., *Synthesis of Polynorbornene-poly(ethylene-co-propylene) Diblock Copolymers*, Polymeric Materials Science and Engineering, 1998, vol. 78, pp. 158-159.
Xu et al., *Ethylene Copolymerization with 1-Octene Using a 2-Methylbenz[e]indenyl-Based ansa-Monocyclopentadienylamido Complex and Methylaluminoxane Catalyst*, Macromolecules, 1998, vol. 31, pp. 4724-4729.
Nalini et al., *"Thermoplastic Polyolefin Nanocomposites: Effect of Mechanical, Thermal, and Morphological Properties"*, Journal of Reinforced Plastics and Composites, 2011, vol. 30, No. 4, pp. 319-324.
Olewnik et al., *"Thermal Properties of New Composites Based on Nanoclay, Polyethylene and Polypropylene"*, Journal of Thermal Analysis and Calorimetry, 2010, vol. 101, No. 1, pp. 323-329.
Sharma et al., *"Polypropylene Nanocomposite Film: A Critical Evaluation on the Effect of Nanoclay on the Mechanical, Thermal, and Morphological Behavior"*, Journal of Applied Polymer Science, 2010, vol. 115, No. 6, pp. 3463-3473.
Sayed et al., *Novel Macromolecules Containing Sym-tetrazine Rings and Their Subsequent Reactions Through Click Modifications*, Polymer Preprints, 2008, vol. 49, No. 1, pp. 188-189.
Chen et al., *Synthesis of Star-Shaped Poly(ε-caprolactone)-b-Poly-(styrene) Block Copolymer by Combining Ring-Opening Polymerization and Atom Transfer Radical Polymerization*, Journal of Macromolecular Science, Part A: Pure and Applied Chemistry, 2005, vol. 42, pp. 1247-1257.
Chen et al., *Study on Synthesis of Star-Shaped Poly(ethylene oxide) by Atom Transfer Radical Polymerization*, Journal of Macromolecular Science, Part A: Pure and Applied Chemistry, 2006, vol. 43, pp. 269-277.
Hoogenboom et al., *(Metallo)supramolecular Click Chemistry Versus Click Chemistry in Polymer Science*, Polymer Preprints, 2007, vol. 48, No. 2, pp. 685-686.
McLean et al., *The 'Inverse Electron-Demand' Diels-Alder Reaction in Polymer Synthesis. Part 3. Model Diels-Alder Reactions of some Bis(1,2,4-triazines) with Dienophiles and some Bis-dienophiles with Heterocyclic Dienes*, Journal of Chem. Research, 1996, vol. S, pp. 448-449.
Reiser, *Oxazoline: Chirale Synthesebausteine, Auxiliare und Liganden*, Nachr. Chem. Tech. Lab., 1996, vol. 44, Nos. 7/8, pp. 744-750 (No Translation or Abstract).
Sagot et al., *Synthesis of Linear and Hyperbranched Tetrazine-based Polyhetarylene Assemblies with High Nitrogen Content*, Tetrahedron, 2007, vol. 63, pp. 11189-11194.
Stoicescu-Gravat et al., *Nouveaux Polymeres Obtenus Par Polyheterocyclisation, Poly-1,2,4,5-tetrazines et Poly-1,2,4-triazoles*, Revue Roumaine de Chimie, 1966, vol. 11, pp. 1127-1134 (No Translation or Abstract).
Warrener et al., *Fundamental Principles of BLOCK Design and Assembly in the Production of Large, Rigid Molecules with Functional Unites (Effectors) Precisely Located on a Carbocyclic Framework*, Synlett, 1998, vol. 29, No. 33, pp. 566-573.

\* cited by examiner

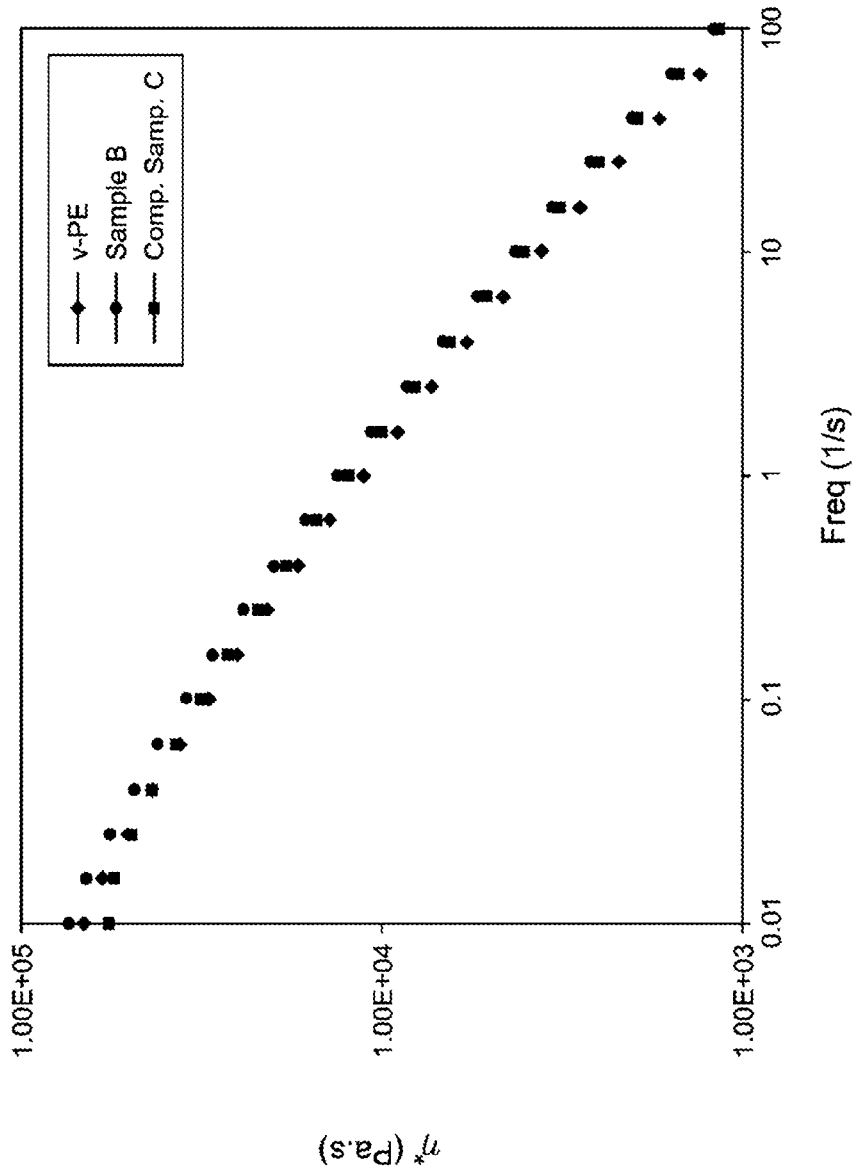

FTIR spectrum for 3,6-Di-2-pyridyl-1,2,4,5-tetrazine

Wavenumbers (cm-1)

Partial FTIR spectrum of Sample B compared to Comparative Sample C

Freq (1/cm)

FUNCTIONALIZED POLYMERS AND OLIGOMERS

BACKGROUND OF THE INVENTION

Polyolefins are non-polar products which typically have a poor affinity with traditional materials such as for example, glass and metals in general, and are incompatible with polar synthetic polymers such as polyesters and polyamides. The ability to functionalize and therefore modify these typically chemically inert polyolefins has been highly sought after. Furthermore, the ability to efficiently and reproducibly functionalize materials such as polyethylene, polypropylene, and related copolymers with a reactive group that could be further utilized in numerous processes and end uses is particularly desirable.

Various methods to functionalize polyolefins are known. However, such methods are often characterized as tedious, time consuming, typically require air/moisture sensitive chemicals and are generally not efficient.

Examples of processes to functionalize polyolefins include the use of free radical chemistry in the reactor, such as in high pressure reactors to create ethylene-vinyl acetate type copolymers. These processes often do not provide adequate control over the number of functional groups added to the polymer.

Examples of processes to functionalize polyolefins post polymerization include grafting, wherein the polyolefin is contacted with maleic anhydride or a similar grafting material, typically in an extruder. Such processes are difficult to control and tend to cross-link the polymer, thereby changing the properties of the functionalized polymer.

Functionalization in solution is also possible, but this process is also difficult to control and tends to cross-link the polymer. Functionalization in solution also requires the additional step of solvent removal.

Accordingly, there is a need for new types of functionalized polymers and efficient, controllable, and benign methods to produce the same.

SUMMARY OF THE INVENTION

The present disclosure relates to a functionalized polyolefin. In an embodiment, a functionalized polyolefin comprises one or more pyridazine moieties according to the following formulae:

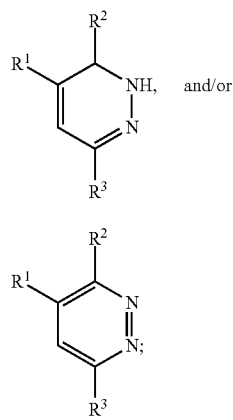

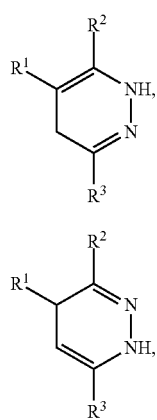

wherein $R^1$ comprises a polyolefin chain attached to the pyridazine moiety through an aliphatic linkage, and wherein $R^2$ and $R^3$ independently comprise H or one or more functional groups comprising atoms from Groups 13, 14, 15, 16, and 17 of the Periodic Table of Elements, or a combination thereof.

The present disclosure further relates to a polyolefin comprising one or more pyridazine moieties according to the following formulae:

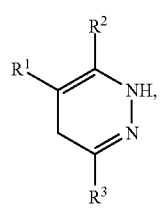

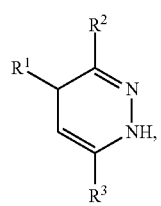

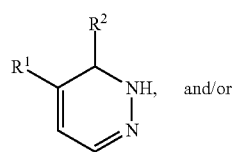

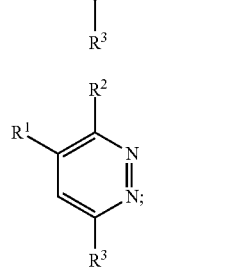

wherein $R^1$ comprises a polyolefin chain attached to the pyridazine moieties through an aliphatic linkage, and wherein $R^2$ and $R^3$ independently comprise H or one or more functional groups comprising atoms from Groups 13, 14, 15, 16, and 17 of the Periodic Table of Elements, or combinations thereof, wherein the pyridazine moiety is the cyclo-addition reaction product of a non-aromatic carbon-carbon double bond attached to a backbone of the polyolefin chain through an aliphatic linkage, and a substituted or unsubstituted tetrazine.

The present disclosure further relates to a method comprising:
contacting a first polyolefin comprising at least one non-aromatic carbon-carbon double bond with a substituted or unsubstituted tetrazine at a temperature and for a period of time sufficient to produce a second polyolefin comprising one or more pyridazine moieties according to the following formulae:

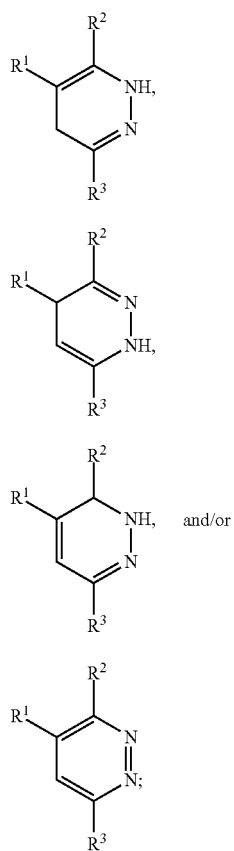

wherein $R^1$ comprises the first polyolefin attached to the pyridazine moiety through an aliphatic linkage, and wherein $R^2$ and $R^3$ independently comprise H or one or more functional groups comprising atoms from Groups 13, 14, 15, 16, and 17 of the Periodic Table of Elements, or a combination thereof.

BRIEF DESCRIPTION OF THE DRAWINGS

FIG. 2 is a complex viscosity versus frequency plot of vinyl terminated polyethylene, a functionalized polyolefin according to an embodiment of this invention, and a Comparative Sample.

DETAILED DESCRIPTION

Figure 1A:
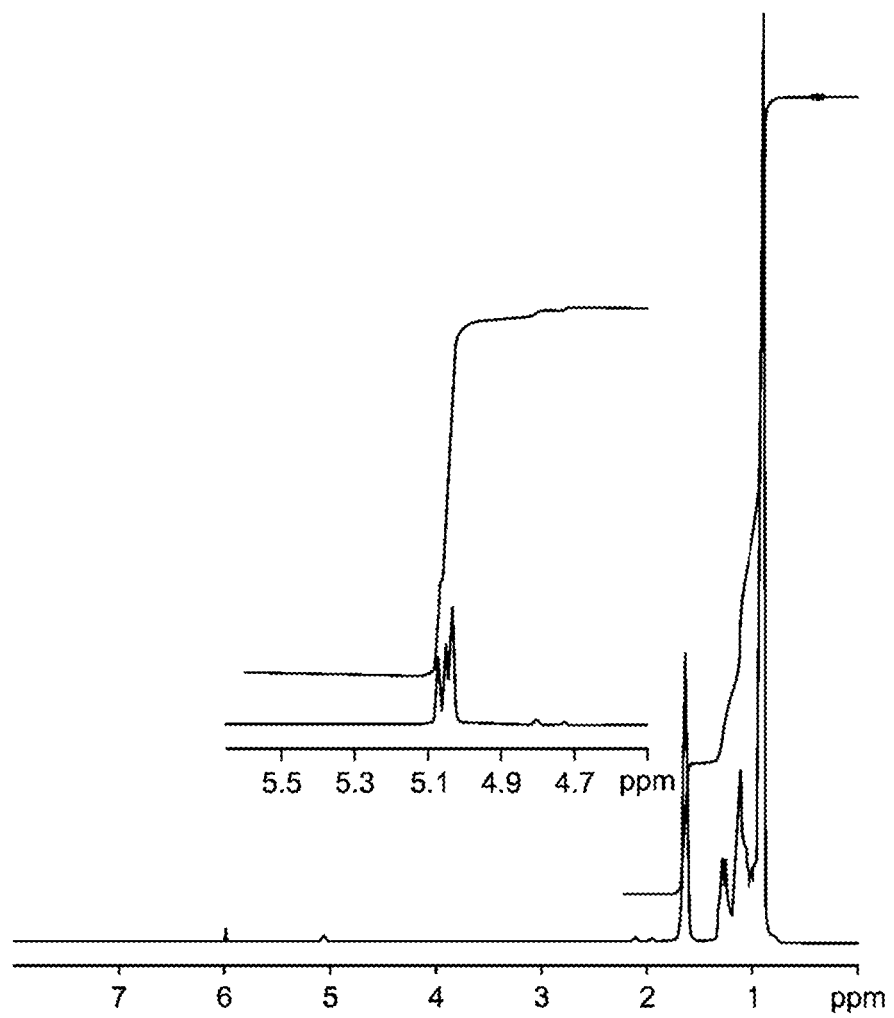
FIG. 1A is a proton nuclear magnetic resonance ($^1$H NMR) spectrum of a vinyl terminated polypropylene.

In the structures depicted throughout this specification and the claims, a solid line indicates a bond, and an arrow indicates that the bond may be dative.

As used herein, the new notation for the Periodic Table Groups is used as described in *Chemical and Engineering News*, 63(5), 27 (1985).

The term "substituted" means that a hydrogen group has been replaced with a hydrocarbyl group, a heteroatom, or a heteroatom containing group. For example, methyl cyclopentadiene (Cp) is a Cp group substituted with a methyl group and ethyl alcohol is an ethyl group substituted with an —OH group.

The terms "hydrocarbyl radical," "hydrocarbyl," and "hydrocarbyl group" are used interchangeably throughout this document. Likewise, the terms "functional group," "group," and "substituent" are also used interchangeably in this document. For purposes of this disclosure, "hydrocarbyl radical" is defined to be $C_1$ to $C_{20}$ radicals, that may be linear, branched, or cyclic (aromatic or non-aromatic); and may include substituted hydrocarbyl radicals as defined herein. In an embodiment, a functional group may comprise a hydrocarbyl radical, a substituted hydrocarbyl radical, or a combination thereof.

Substituted hydrocarbyl radicals are radicals in which at least one hydrogen atom has been substituted with a heteroatom or heteroatom containing group, or with atoms from Groups 13, 14, 15, 16, and 17 of the Periodic Table of Elements, or a combination thereof, or with at least one functional group, such as halogen (Cl, Br, I, F), $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$, and the like or where at least one heteroatom has been inserted within the hydrocarbyl radical, such as halogen (Cl, Br, I, F), O, S, Se, Te, $NR*$, $PR*$, $AsR*$, $SbR*$, $BR*$, $SiR*_2$, $GeR*_2$, $SnR*_2$, $PbR*_2$, and the like, where $R*$ is, independently, hydrogen or a hydrocarbyl radical, or any combination thereof.

In an embodiment, the hydrocarbyl radical is independently selected from methyl, ethyl, ethenyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated, and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl, and alkynyl radicals listed include all isomers including, where appropriate, cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (analogous substituted cyclobutyls and cyclopropyls); and butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (cyclobutenyls and cyclopropenyls). Cyclic compounds having substitutions include all isomer forms, for example, methylphenyl would include ortho-methylphenyl, meta-methylphenyl, and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, including, but not limited to, ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is a polymer having a low molecular weight. In some embodiments, an oligomer has an Mn of 21,000 g/mol or less (e.g., 2,500 g/mol or less); in other embodiments, an oligomer has a low number of mer units (such as 75 mer units or less).

An "alpha-olefin" is an olefin having a double bond at the alpha (or 1-) position. A "linear alpha-olefin" or "LAO" is an olefin with a double bond at the alpha position and a linear hydrocarbon chain. A "polyalphaolefin" or "PAO" is a polymer having two or more alpha-olefin units. For the purposes of this disclosure, the term "α-olefin" includes $C_2$-$C_{20}$ olefins. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

For purposes herein, a polymer or polymeric chain comprises a concatenation of carbon atoms bonded to each other in a linear or a branched chain, which is referred to herein as the backbone of the polymer (e.g., polyethylene). The polymeric chain may further comprise various pendent groups attached to the polymer backbone which were present on the monomers from which the polymer was produced. These pendent groups are not to be confused with branching of the polymer backbone, the difference between pendent side chains and both short and long chain branching being readily understood by one of skill in the art.

The terms "catalyst" and "catalyst compound" are defined to mean a compound capable of initiating catalysis. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is a combination of at least one catalyst compound, an optional activator, an optional co-activator, and an optional support material, where the system can polymerize monomers to polymer. For the purposes of this invention and the claims thereto, when catalyst systems are described as comprising neutral stable forms of the components, it is well understood by one of ordinary skill in the art, that the ionic form of the component is the form that reacts with the monomers to produce polymers.

An "anionic ligand" is a negatively charged ligand which donates one or more pairs of electrons to a metal ion. A "neutral donor ligand" is a neutrally charged ligand which donates one or more pairs of electrons to a metal ion.

A "scavenger" is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the catalyst compound to form an alkylated catalyst compound, also referred to as an alkylated invention compound.

A propylene polymer is a polymer having at least 50 mol % of propylene. As used herein, Mn is number average molecular weight as determined by proton nuclear magnetic resonance spectroscopy ($^1$H NMR), as described in the Examples, unless stated otherwise, Mw is weight average molecular weight as determined by gel permeation chromatography (GPC), Mz is z average molecular weight as determined by GPC as described below, wt % is weight percent, and mol % is mole percent. Molecular weight distribution (MWD) is defined to be Mw divided by Mn ($^1$H NMR). Unless otherwise noted, all molecular weight units, e.g., Mw, Mn, Mz, are g/mol.

The following abbreviations may be used through this specification: Me is methyl, Ph is phenyl, Et is ethyl, Pr is propyl, iPr is isopropyl, n-pr is normal propyl, Bu is butyl, iBu is isobutyl, tBu is tertiary butyl, p-tBu is para-tertiary butyl, nBu is normal butyl, TMS is trimethylsilyl, TIBAL is triisobutylaluminum, TNOAL is triisobutyl n-octylaluminum, MAO is methylalumoxane, pMe is para-methyl, Ar* is 2,6-diisopropylaryl, Bz is benzyl, THF is tetrahydrofuran, RT is room temperature which is defined as 25° C. unless otherwise specified, and tol is toluene.

The term "phr" is parts per hundred rubber or "parts", and is a measure common in the art wherein components of a composition are measured by weight, relative to a total weight of all of the elastomer components. The total phr or parts for all rubber components, whether one, two, three, or more different rubber components is present in a given recipe is always defined as 100 phr. All other non-rubber components are ratioed by weight against the 100 parts of rubber and are expressed in phr. This way one can easily compare, for example, the levels of curatives or filler loadings, etc., between different compositions based on the same relative proportion of rubber without the need to recalculate percents for every component after adjusting levels of only one, or more, component(s).

The inventors have surprisingly found new methods of modifying polyolefins having one or more carbon-carbon double bond to produce new polyolefins having a pyridazine moiety. Preferably, the carbon-carbon double bond of the polyolefin is a vinyl group, but it is within the scope of this invention that polyolefins having other double bonds (such as vinylidenes or internal double bonds) may be useful in embodiments herein.

Advantageously, these inventive methods are industrially benign, utilizing materials that are not explosive or air or moisture sensitive. The methods are also industrially cost-effective, as they require no catalyst. Even more advantageously, these reactions are environmentally benign as they produce nitrogen, which is volatile, inert, and non-toxic, as the only byproduct.

In an embodiment, the polyolefins of the present invention are produced via "click" chemistry, wherein selected reactions are classified as click chemistry for being specific, wide in scope, result in high yields, and which generate only safe byproducts, which may be processed under simple conditions, with readily available starting materials and without any solvent, consistent with the term "click chemistry" as is commonly known in the art. In some embodiments, the present disclosure is directed to a polyolefin comprising one or more pyridazine moieties according to the following formulae:

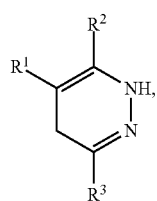

(I)

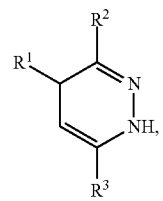

(II)

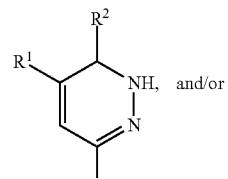

(III)

and/or

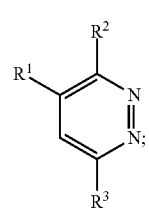

(IV)

wherein $R^1$ comprises a polyolefin chain attached to the pyridazine moiety through an aliphatic linkage, and wherein $R^2$ and $R^3$ each comprise hydrogen (H) or one or more functional groups comprising atoms from Groups 13, 14, 15, 16, and 17 of the Periodic Table of Elements, or a combination thereof. As used herein "an aliphatic linkage" includes a direct linkage to the aliphatic polyolefin. In an embodiment, the aliphatic linkage is comprised of non-aromatic carbon-carbon bonds connecting the pyridazine ring to the backbone of the polymeric chain.

In an embodiment, the pyridazine moiety is directly bonded to the backbone of the polymer chain. In an embodiment, the pyridazine moiety is bonded to the backbone of the polymer chain through a chain comprising one or more carbon-carbon single bonds, double bonds, carbon-oxygen bonds, e.g., ether bonds, carbon-nitrogen bonds, e.g., amine bonds; carbon-sulfur bonds, e.g., thio-ether bonds; carbon-phosphorous bonds, or a combination thereof. In an embodiment, the pyridazine moiety is a terminal moiety of the polyolefin chain. In an embodiment, the pyridazine moiety may be attached to the polymer backbone through a pendant group attached to the polymer backbone.

In an embodiment, the pyridazine moiety is attached to the polymer backbone subject to the proviso that the pyridazine moiety is not attached to the polymer backbone through a chain comprising an aromatic bond in the linkage connecting the pyridazine ring to the polymer backbone. Accordingly, a polymer comprising divinyl benzene or other divinyl aromatic monomers, wherein the pyridazine moiety is attached to the polymer backbone pendent to an aromatic ring is specifically not included as an embodiment for purposes herein. In embodiments herein, in polymers comprising divinyl benzene or other divinyl aromatic monomers, pyridazine moieties attached to the polymer backbone pendent to aromatic rings are absent.

In an embodiment, the polyolefin chain comprises a $C_{2-20}$ poly-alpha-olefin having a Mw of greater than or equal to about 2500 g/mol (preferably greater than or equal to about 3000 g/mol, greater than or equal to 3500 g/mol, and greater than or equal to 4000 g/mol).

In an embodiment, the polyolefin chain comprises ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane, or a combination thereof.

In an embodiment, the polyolefin chain comprises ethylene, propylene, butene, hexene, octene, or a combination thereof.

In an embodiment of the present invention, the polyolefin chain ($R^1$) in Formula (I) is derived from polyethylene, polypropylene, polybutadiene, butyl rubber, or vinyl terminated macromonomers. In an embodiment, the polyolefin chain ($R^1$) is derived from an ethylene-diene copolymer, which may include ethylene-norbornene copolymers, and the like.

A "vinyl terminated macromonomer," as used herein, refers to one or more of:

(i) a vinyl terminated polymer having at least 5% allyl chain ends (preferably 15%, 20%, 30%, 40%, 50%, 60%, 70%, 80%, 90%, 95%, 98%, or 99%);

(ii) a vinyl terminated polymer having an Mn of at least 200 g/mol (measured by $^1$H NMR) comprising of one or more $C_4$ to $C_{40}$ higher olefin derived units, where the higher olefin polymer comprises substantially no propylene derived units; and wherein the higher olefin polymer has at least 5% allyl chain ends;

(iii) a copolymer having an Mn of 300 g/mol or more (measured by $^1$H NMR) comprising (a) from about 20 mol % to about 99.9 mol % of at least one $C_5$ to $C_{40}$ higher olefin, and (b) from about 0.1 mol % to about 80 mol % of propylene, wherein the higher olefin copolymer has at least 40% allyl chain ends;

(iv) a copolymer having an Mn of 300 g/mol or more (measured by $^1$H NMR), and comprises (a) from about 80 mol % to about 99.9 mol % of at least one $C_4$ olefin, (b) from about 0.1 mol % to about 20 mol % of propylene; and wherein the vinyl terminated macromonomer has at least 40% allyl chain ends relative to total unsaturation;

(v) a co-oligomer having an Mn of 300 g/mol to 30,000 g/mol (measured by $^1$H NMR) comprising 10 mol % to 90 mol % propylene and 10 mol % to 90 mol % of ethylene, wherein the oligomer has at least X % allyl chain ends (relative to total unsaturations), where: 1) X=(−0.94*(mol % ethylene incorporated)+100), when 10 mol % to 60 mol % ethylene is present in the co-oligomer, 2) X=45, when greater than 60 mol % and less than 70 mol % ethylene is present in the co-oligomer, and 3) X=(1.83*(mol % ethylene incorporated)−83), when 70 mol % to 90 mol % ethylene is present in the co-oligomer;

(vi) a propylene oligomer, comprising more than 90 mol % propylene and less than 10 mol % ethylene wherein the oligomer has: at least 93% allyl chain ends, a number average molecular weight (Mn) of about 500 g/mol to about 20,000 g/mol, an isobutyl chain end to allylic vinyl group ratio of 0.8:1 to 1.35:1.0, and less than 100 ppm aluminum;

(vii) a propylene oligomer, comprising: at least 50 mol % propylene and from 10 mol % to 50 mol % ethylene, wherein the oligomer has: at least 90% allyl chain ends, an Mn of about 150 g/mol to about 10,000 g/mol, and an isobutyl chain end to allylic vinyl group ratio of 0.8:1 to 1.2:1.0, wherein monomers having four or more carbon atoms are present at from 0 mol % to 3 mol %;

(viii) a propylene oligomer, comprising: at least 50 mol % propylene, from 0.1 mol % to 45 mol % ethylene, and from 0.1 mol % to 5 mol % $C_4$ to $C_{12}$ olefin, wherein the oligomer has: at least 90% allyl chain ends, an Mn of about 150 g/mol to about 10,000 g/mol, and an isobutyl chain end to allylic vinyl group ratio of 0.8:1 to 1.35:1.0;

(ix) a propylene oligomer, comprising: at least 50 mol % propylene, from 0.1 mol % to 45 mol % ethylene, and from 0.1 mol % to 5 mol % diene, wherein the oligomer has: at least 90% allyl chain ends, an Mn of about 150 g/mol to about 10,000 g/mol, and an isobutyl chain end to allylic vinyl group ratio of 0.7:1 to 1.35:1.0; and (x) a homo-oligomer, comprising propylene, wherein the oligomer has: at least 93% allyl chain ends, an Mn of about 500 g/mol to about 20,000 g/mol, an isobutyl chain end to allylic vinyl group ratio of 0.8:1 to 1.2:1.0, and less than 1400 ppm aluminum.

In some embodiments, the vinyl terminated macromonomer has an Mn of at least 200 g/mol, (e.g., 200 g/mol to 100,000 g/mol, e.g., 200 g/mol to 75,000 g/mol, e.g., 200 g/mol to 60,000 g/mol, e.g., 300 g/mol to 60,000 g/mol, or e.g., 750 g/mol to 30,000 g/mol) (measured by $^1$H NMR) and comprise one or more (e.g., two or more, three or more, four or more, and the like) $C_4$ to $C_{40}$ (e.g., $C_4$ to $C_{30}$, $C_4$ to $C_{20}$, or $C_4$ to $C_{12}$, e.g., butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof) olefin derived units, where the vinyl terminated macromonomer comprises substantially no propylene derived units (e.g., less than 0.1 wt % propylene, e.g., 0 wt %); and wherein the vinyl terminated macromonomer has at least 5% (at least 10%, at least 15%, at least 20%, at least 30%, at least 40%, at least 50%, at least 60%, at least 70%; at least 80%, at least 90%, or at least 95%) allyl chain ends (relative to total unsaturation); and optionally, an allyl chain end to vinylidene chain end ratio of 1:1 or greater (e.g., greater than 2:1, greater than 2.5:1, greater than 3:1, greater than 5:1, or greater than 10:1); and even further optionally, e.g., substantially no isobutyl chain ends (e.g., less than 0.1 wt % isobutyl chain ends). In some embodiments, the vinyl terminated macromonomers may also comprise ethylene derived units, e.g., at least 5 mol % ethylene (e.g., at least 15 mol % ethylene, e.g., at least 25 mol % ethylene, e.g., at least 35 mol % ethylene, e.g., at least 45 mol % ethylene, e.g., at least 60 mol % ethylene, e.g., at least 75 mol % ethylene, or e.g., at least 90 mol % ethylene). Such vinyl terminated macromonomers are further described in U.S. Ser. No. 13/072,288, which is hereby incorporated by reference.

In some embodiments, the vinyl terminated macromonomers may have an Mn (measured by $^1$H NMR) of greater than 200 g/mol (e.g., 300 g/mol to 60,000 g/mol, 400 g/mol to 50,000 g/mol, 500 g/mol to 35,000 g/mol, 300 g/mol to 15,000 g/mol, 400 g/mol to 12,000 g/mol, or 750 g/mol to 10,000 g/mol), and comprise:

(a) from about 20 mol % to 99.9 mol % (e.g., from about 25 mol % to about 90 mol %, from about 30 mol % to about 85 mol %, from about 35 mol % to about 80 mol %, from about 40 mol % to about 75 mol %, or from about 50 mol % to about 95 mol %) of at least one $C_5$ to $C_{40}$ (e.g., $C_6$ to $C_{20}$) higher olefin; and (b) from about 0.1 mol % to 80 mol % (e.g., from about 5 mol % to 70 mol %, from about 10 mol % to about 65 mol %, from about 15 mol % to about 55 mol %, from about 25 mol % to about 50 mol %, or from about 30 mol % to about 80 mol %) of propylene;

wherein the vinyl terminated macromonomer has at least 40% allyl chain ends (e.g., at least 50% allyl chain ends, at least 60% allyl chain ends, at least 70% allyl chain ends, or at least 80% allyl chain ends, at least 90% allyl chain ends, at least 95% allyl chain ends) relative to total unsaturation; and, optionally, an isobutyl chain end to allyl chain end ratio of less than 0.70:1, less than 0.65:1, less than 0.60:1, less than 0.50:1, or less than 0.25:1; and further optionally, an allyl chain end to vinylidene chain end ratio of greater than 2:1 (e.g., greater than 2.5:1, greater than 3:1, greater than 5:1, or greater than 10:1); and even further optionally, an allyl chain end to vinylene ratio is greater than 1:1 (e.g., greater than 2:1 or greater than 5:1). Such macromonomers are further described in U.S. Ser. No. 13/072,249, hereby incorporated by reference.

In another embodiment, the vinyl terminated macromonomer has an Mn of 300 g/mol or more (measured by $^1$H NMR, e.g., 300 g/mol to 60,000 g/mol, 400 g/mol to 50,000 g/mol, 500 g/mol to 35,000 g/mol, 300 g/mol to 15,000 g/mol, 400 g/mol to 12,000 g/mol, or 750 g/mol to 10,000 g/mol), and comprises:

(a) from about 80 mol % to about 99.9 mol % of at least one $C_4$ olefin, e.g., about 85 mol % to about 99.9 mol %, e.g., about 90 mol % to about 99.9 mol %;

(b) from about 0.1 mol % to about 20 mol % of propylene, e.g., about 0.1 mol % to about 15 mol %, e.g., about 0.1 mol % to about 10 mol %; and wherein the vinyl terminated macromonomer has at least 40% allyl chain ends (e.g., at least 50% allyl chain ends, at least 60% allyl chain ends, at least 70% allyl chain ends, or at least 80% allyl chain ends, at least 90% allyl chain ends, at least 95% allyl chain ends) relative to total unsaturation, and in some embodiments, an isobutyl chain end to allyl chain end ratio of less than 0.70:1, less than 0.65:1, less than 0.60:1, less than 0.50:1, or less than 0.25:1, and in further embodiments, an allyl chain end to vinylidene group ratio of more than 2:1, more than 2.5:1, more than 3:1, more than 5:1, or more than 10:1. Such macromonomers are also further described in U.S. Ser. No. 13/072,249, which is hereby incorporated by reference.

In other embodiments, the vinyl terminated macromonomer is a propylene co-oligomer having an Mn of 300 g/mol to 30,000 g/mol as measured by $^1$H NMR (e.g., 400 g/mol to 20,000 g/mol, e.g., 500 g/mol to 15,000 g/mol, e.g., 600 g/mol to 12,000 g/mol, e.g., 800 g/mol to 10,000 g/mol, e.g., 900 g/mol to 8,000 g/mol, e.g., 900 g/mol to 7,000 g/mol), comprising 10 mol % to 90 mol % propylene (e.g., 15 mol % to 85 mol %, e.g., 20 mol % to 80 mol %, e.g., 30 mol % to 75 mol %, e.g., 50 mol % to 90 mol %) and 10 mol % to 90 mol % (e.g., 85 mol % to 15 mol %, e.g., 20 mol % to 80 mol %, e.g., 25 mol % to 70 mol %, e.g., 10 mol % to 50 mol %) of one or more alpha-olefin comonomers (e.g., ethylene, butene, hexene, or octene, e.g., ethylene), wherein the oligomer has at least X % allyl chain ends (relative to total unsaturations), where: 1) X=(−0.94 (mol % ethylene incorporated)+100 {alternately 1.20 (−0.94 (mol % ethylene incorporated)+100), alternately 1.50(−0.94 (mol % ethylene incorporated)+100)}), when 10 mol % to 60 mol % ethylene is present in the co-oligomer; 2) X=45 (alternately 50, alternately 60), when greater than 60 mol % and less than 70 mol % ethylene is present in the co-oligomer; and 3) X=(1.83*(mol % ethylene incorporated)−83, {alternately 1.20 [1.83*(mol % ethylene incorporated)-83], alternately 1.50 [1.83*(mol % ethylene incorporated)-83]}), when 70 mol % to 90 mol % ethylene is present in the co-oligomer. Such macromonomers are further described in U.S. Ser. No. 12/143,663, which is hereby incorporated by reference.

In other embodiments, the vinyl terminated macromonomer is a propylene oligomer, comprising more than 90 mol % propylene (e.g., 95 mol % to 99 mol %, e.g., 98 mol % to 9 mol %) and less than 10 mol % ethylene (e.g., 1 mol % to 4 mol %, e.g., 1 mol % to 2 mol %), wherein the oligomer has: at least 93% allyl chain ends (e.g., at least 95%, e.g., at least 97%, e.g., at least 98%); a number average molecular weight (Mn) of about 400 g/mol to about 30,000 g/mol, as measured by $^1$H NMR (e.g., 500 g/mol to 20,000 g/mol, e.g., 600 g/mol to 15,000 g/mol, e.g., 700 g/mol to 10,000 g/mol, e.g., 800 g/mol to 9,000 g/mol, e.g., 900 g/mol to 8,000 g/mol, e.g., 1,000 g/mol to 6,000 g/mol); an isobutyl chain end to allylic vinyl group ratio of 0.8:1 to 1.35:1.0, and less than 1400 ppm aluminum, (e.g., less than 1200 ppm, e.g., less than 1000 ppm, e.g., less than 500 ppm, e.g., less than 100 ppm). Such macromonomers are further described in U.S. Ser. No. 12/143,663.

In other embodiments, the vinyl terminated macromonomer is a propylene oligomer, comprising: at least 50 mol % (e.g., 60 mol % to 90 mol %, e.g., 70 mol % to 90 mol %) propylene and from 10 mol % to 50 mol % (e.g., 10 mol % to 40 mol %, e.g., 10 mol % to 30 mol %) ethylene, wherein the oligomer has: at least 90% allyl chain ends (e.g., at least 91%, e.g., at least 93%, e.g., at least 95%, e.g., at least 98%); an Mn of about 150 g/mol to about 20,000 g/mol, as measured by $^1$H NMR (e.g., 200 g/mol to 15,000 g/mol, e.g., 250 g/mol to 15,000 g/mol, e.g., 300 g/mol to 10,000 g/mol, e.g., 400 g/mol to 9,500 g/mol, e.g., 500 g/mol to 9,000 g/mol, e.g., 750 g/mol to 9,000 g/mol); and an isobutyl chain end to allylic vinyl group ratio of 0.8:1 to 1.3:1.0, wherein monomers having four or more carbon atoms are present at from 0 mol % to 3 mol % (e.g., at less than 1 mol %, e.g., less than 0.5 mol %, e.g., at 0 mol %). Such macromonomers are further described in U.S. Ser. No. 12/143,663.

In other embodiments, the vinyl terminated macromonomer is a propylene oligomer, comprising: at least 50 mol % (e.g., at least 60 mol %, e.g., 70 mol % to 99.5 mol %, e.g., 80 mol % to 99 mol %, e.g., 90 mol % to 98.5 mol %) propylene, from 0.1 mol % to 45 mol % (e.g., at least 35 mol %, e.g., 0.5 mol % to 30 mol %, e.g., 1 mol % to 20 mol %, e.g., 1.5 mol % to 10 mol %) ethylene, and from 0.1 mol % to 5 mol % (e.g., 0.5 mol % to 3 mol %, e.g., 0.5 mol % to 1 mol %) $C_4$ to $C_{12}$ olefin (such as butene, hexene, or octene, e.g., butene), wherein the oligomer has: at least 90% allyl chain ends (e.g., at least 91%, e.g., at least 93%, e.g., at least 95%, e.g., at least 98%); a number average molecular weight (Mn) of about 150 g/mol to about 15,000 g/mol, as measured by $^1$H NMR (e.g., 200 g/mol to 12,000 g/mol, e.g., 250 g/mol to 10,000 g/mol, e.g., 300 g/mol to 10,000 g/mol, e.g., 400 g/mol to 9500 g/mol, e.g., 500 g/mol to 9,000 g/mol, e.g., 750 g/mol to 9,000 g/mol); and an isobutyl chain end to allylic vinyl group ratio of 0.8:1 to 1.35:1.0. Such macromonomers are further described in U.S. Ser. No. 12/143,663.

In other embodiments, the vinyl terminated macromonomer is a propylene oligomer, comprising: at least 50 mol % (e.g., at least 60 mol %, e.g., 70 mol % to 99.5 mol %, e.g., 80 mol % to 99 mol %, e.g., 90 mol % to 98.5 mol %) propylene, from 0.1 mol % to 45 mol % (e.g., at least 35 mol %, e.g., 0.5 mol % to 30 mol %, e.g., 1 mol % to 20 mol %, e.g., 1.5 mol % to 10 mol %) ethylene, and from 0.1 mol % to 5 mol % (e.g., 0.5 mol % to 3 mol %, e.g., 0.5 mol % to 1 mol %) diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the oligomer has at least 90% allyl chain ends (e.g., at least 91%, e.g., at least 93%, e.g., at least 95%, e.g., at least 98%); a number average molecular weight (Mn) of about 150 g/mol to about 20,000 g/mol, as measured by $^1$H NMR (e.g., 200 g/mol to 15,000 g/mol, e.g., 250 g/mol to 12,000 g/mol, e.g., 300 g/mol to 10,000 g/mol, e.g., 400 g/mol to 9,500 g/mol, e.g., 500 g/mol to 9,000 g/mol, e.g., 750 g/mol to 9,000 g/mol); and an isobutyl chain end to allylic vinyl group ratio of 0.7:1 to 1.35:1.0. Such macromonomers are further described in U.S. Ser. No. 12/143,663.

In other embodiments, the vinyl terminated macromonomer is a propylene homo-oligomer, comprising propylene and less than 0.5 wt % comonomer, e.g., 0 wt % comonomer, wherein the oligomer has:
i) at least 93% allyl chain ends (e.g., at least 95%, e.g., at least 96%, e.g., at least 97%, e.g., at least 98%, e.g., at least 99%);
ii) a number average molecular weight (Mn) of about 500 g/mol to about 20,000 g/mol, as measured by $^1$H NMR (e.g., 500 g/mol to 15,000 g/mol, e.g., 700 g/mol to 10,000 g/mol, e.g., 800 g/mol to 8,000 g/mol, e.g., 900 g/mol to 7,000 g/mol, e.g., 1,000 g/mol to 6,000 g/mol, e.g., 1,000 g/mol to 5,000 g/mol);
iii) an isobutyl chain end to allylic vinyl group ratio of 0.8:1 to 1.3:1.0; and
iv) less than 1400 ppm aluminum, (e.g., less than 1200 ppm, e.g., less than 1000 ppm, e.g., less than 500 ppm, e.g., less than 100 ppm). Such macromonomers are also further described in U.S. Ser. No. 12/143,663.

The vinyl terminated macromonomers may be homopolymers, copolymers, terpolymers, and so on. Any vinyl terminated macromonomers described herein has one or more of:
(i) an isobutyl chain end to allylic vinyl group ratio of 0.8:1 to 1.3:1.0;
(ii) an allyl chain end to vinylidene chain end ratio of greater than 2:1 (e.g., greater than 2.5:1, greater than 3:1, greater than 5:1, or greater than 10:1);
(iii) an allyl chain end to vinylene ratio is greater than 1:1 (e.g., greater than 2:1 or greater than 5:1); and
(iv) at least 5% allyl chain ends (preferably 15%, 20%, 30%, 40%, 50%, 60%, 70%, 80%, 90%, 95%, 98%, or 99%).

Vinyl terminated macromonomers generally have a saturated chain end (or terminus) and/or an unsaturated chain end or terminus. The unsaturated chain end of the vinyl terminated macromonomer comprises an "allyl chain end" or a "3-alkyl" chain end. An allyl chain end is represented by $CH_2CH=CH_2-$, as shown in the formula:

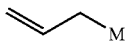

where M represents the polymer chain. "Allylic vinyl group," "allyl chain end," "vinyl chain end," "vinyl termination," "allylic vinyl group," and "vinyl terminated" are used interchangeably in the following description. The number of allyl chain ends, vinylidene chain ends, vinylene chain ends, and other unsaturated chain ends is determined using $^1$H NMR at 120° C. using deuterated tetrachloroethane as the solvent on an at least 250 MHz NMR spectrometer, and in selected cases, confirmed by $^{13}$C NMR. Resconi has reported proton and carbon assignments (neat perdeuterated tetrachloroethane used for proton spectra, while a 50:50 mixture of normal and perdeuterated tetrachloroethane was used for carbon spectra; all spectra were recorded at 100° C. on a BRUKER spectrometer operating at 500 MHz for proton and 125 MHz for carbon) for vinyl terminated oligomers in *J. American Chemical Soc.*, 114, 1992, pp. 1025-1032 that are useful herein. Allyl chain ends are reported as a molar percentage of the total number of moles of unsaturated groups (that is, the sum of allyl chain ends, vinylidene chain ends, vinylene chain ends, and the like).

A 3-alkyl chain end (where the alkyl is a $C_1$ to $C_{38}$ alkyl), also referred to as a "3-alkyl vinyl end group" or a "3-alkyl vinyl termination", is represented by the formula:

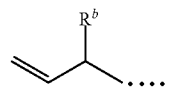

3-Alkyl Vinyl End Group where "●●●●" represents the polyolefin chain and $R^b$ is a $C_1$ to $C_{38}$ alkyl group, or a $C_1$ to $C_{20}$ alkyl group, such as methyl, ethyl, propyl, butyl, pentyl, hexyl, heptyl, octyl, nonyl, decyl, undecyl, dodecyl, and the like. The amount of 3-alkyl chain ends is determined using $^{13}$C NMR as set out below.

$^{13}$C NMR data is collected at 120° C. at a frequency of at least 100 MHz, using a BRUKER 400 MHz NMR spectrometer. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra is acquired with time averaging to provide a signal to noise level adequate to measure the signals of interest. Samples are dissolved in tetrachloroethane-$d_2$ at concentrations between 10 wt % to 15 wt % prior to being inserted into the spectrometer magnet. Prior to data analysis spectra are referenced by setting the chemical shift of the TCE solvent signal to 74.39 ppm. Chain ends for quantization were identified using the signals shown in the table below. N-butyl and n-propyl were not reported due to their low abundance (less than 5%) relative to the chain ends shown in the table below.

| Chain End | $^{13}$C NMR Chemical Shift |
|---|---|
| P~i-Bu | 23-5 to 25.5 and 25.8 to 26.3 ppm |
| E~i-Bu | 39.5 to 40.2 ppm |
| P~Vinyl | 41.5 to 43 ppm |
| E~Vinyl | 33.9 to 34.4 ppm |

The "allyl chain end to vinylidene chain end ratio" is defined to be the ratio of the percentage of allyl chain ends to the percentage of vinylidene chain ends. The "allyl chain end to vinylene chain end ratio" is defined to be the ratio of the percentage of allyl chain ends to the percentage of vinylene chain ends. Vinyl terminated macromonomers typically also have a saturated chain end. In polymerizations where propylene is present, the polymer chain may initiate growth in a propylene monomer, thereby generating an isobutyl chain end. An "isobutyl chain end" is defined to be an end or terminus of a polymer, represented as shown in the formula below:

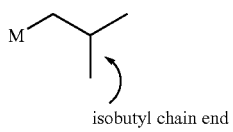

isobutyl chain end where M represents the polymer chain. Isobutyl chain ends are determined according to the procedure set out in WO 2009/155471. The "isobutyl chain end to allylic vinyl group ratio" is defined to be the ratio of the percentage of isobutyl chain ends to the percentage of allyl chain ends.

In polymerizations comprising $C_4$ or greater monomers (or "higher olefin" monomers), the saturated chain end may be a $C_4$ or greater (or "higher olefin") chain end, as shown in the formula below:

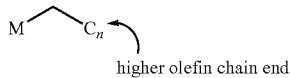

higher olefin chain end where M represents the polymer chain and n is an integer selected from 4 to 40. This is especially true when there is substantially no ethylene or propylene in the polymerization. In an ethylene/($C_4$ or greater monomer) copolymerization, the polymer chain may initiate growth in an ethylene monomer, thereby generating a saturated chain end which is an ethyl chain end. Mn ($^1$H NMR) is determined according to the following NMR method. $^1$H NMR data is collected at either room temperature or 120° C. (for purposes of the claims, 120° C. shall be used) in a 5 mm probe using a Varian spectrometer with a $^1$H frequency of 250 MHz, 400 MHz, or 500 MHz (for the purpose of the claims, a proton frequency of 400 MHz is used). Data are recorded using a maximum pulse width of 45° C., 8 seconds between pulses and signal averaging 120 transients. Spectral signals are integrated and the number of unsaturation types per 1000 carbons is calculated by multiplying the different groups by 1000 and dividing the result by the total number of carbons. Mn is calculated by dividing the total number of unsaturated species into 14,000, and has units of g/mol. The chemical shift regions for the olefin types are defined to be between the following spectral regions.

| Unsaturation Type | Region (ppm) | Number of hydrogens per structure |
|---|---|---|
| Vinyl | 4.95-5.10 | 2 |
| Vinylidene (VYD) | 4.70-4.84 | 2 |
| Vinylene | 5.31-5.55 | 2 |
| Trisubstituted | 5.11-5.30 | 1 |

Mn may also be determined using a GPC-DRI method, as described below. For the purpose of the claims, Mn is determined by $^1$H NMR. Mn, Mw, and Mz may be measured by using a Gel Permeation Chromatography (GPC) method using a High Temperature Size Exclusion Chromatograph (SEC, either from Waters Corporation or Polymer Laboratories), equipped with a differential refractive index detector (DRI). Experimental details, are described in: T. Sun, P. Brant, R. R. Chance, and W. W. Graessley, *Macromolecules*, Volume 34, Number 19, pp. 6812-6820, (2001) and references therein. Three Polymer Laboratories PLgel 10 mm Mixed-B columns are used. The nominal flow rate is 0.5 cm$^3$/min and the nominal injection volume is 300 μL. The various transfer lines, columns and differential refractometer (the DRI detector) are contained in an oven maintained at 135° C. Solvent for the SEC experiment is prepared by dissolving 6 grams of butylated hydroxy toluene as an antioxidant in 4 liters of Aldrich reagent grade 1,2,4 trichlorobenzene (TCB). The TCB mixture is then filtered through a 0.7 μm glass pre-filter and subsequently through a 0.1 μm Teflon filter. The TCB is then degassed with an online degasser before entering the SEC. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/mL at room temperature and 1.324 g/mL at 135° C. The injection concentration is from 1.0 to 2.0 mg/mL, with lower concentrations being used for higher molecular weight samples. Prior to running each sample the DRI detector and the injector are purged. Flow rate in the apparatus is then increased to 0.5 mL/minute, and the DRI is allowed to stabilize for 8 to 9 hours before injecting the first sample. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 135° C. and =690 nm. For purposes of this invention and the claims thereto, (dn/dc)=0.104 for propylene polymers and ethylene polymers, and 0.1 otherwise. Units of parameters used throughout this description of the SEC method are: concentration is expressed in g/cm$^3$, molecular weight is expressed in g/mol, and intrinsic viscosity is expressed in dL/g.

In an embodiment, the polyolefin is derived from a vinyl terminated propylene polymer. In an embodiment, the vinyl terminated propylene polymer is produced using a process comprising: contacting propylene, under polymerization conditions, with a catalyst system comprising an activator and at least one metallocene compound represented by the formula:

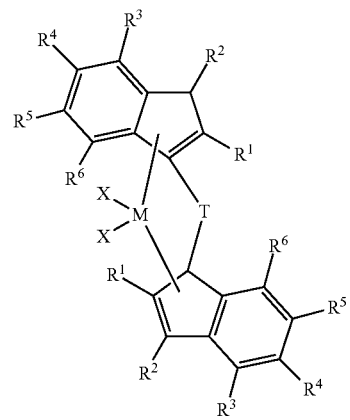

where:
M is hafnium or zirconium;
each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system);

each $R^1$ is, independently, a $C_1$ to $C_{10}$ alkyl group;
each $R^2$ is, independently, a $C_1$ to $C_{10}$ alkyl group;
each $R^3$ is hydrogen;
each $R^4$, $R^5$, and $R^6$, is, independently, hydrogen or a substituted hydrocarbyl or unsubstituted hydrocarbyl group, or a heteroatom;
T is a bridging group; and
further provided that any of adjacent $R^4$, $R^5$, and $R^6$ groups may form a fused ring or multicenter fused ring system where the rings may be aromatic, partially saturated or saturated; and obtaining a propylene polymer having at least 50% allyl chain ends (relative to total unsaturations), as described in co-pending U.S. Ser. No. 13/072,280, filed Mar. 25, 2011, which is incorporated by reference in its entirety herein.

In an embodiment, the vinyl terminated propylene polymer is produced using a process comprising:
1) contacting:
   a) one or more olefins with
   b) a transition metal catalyst compound represented by the formula:

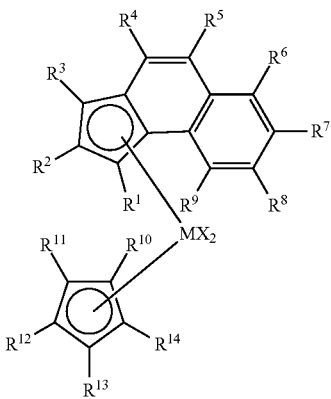

wherein
M is hafnium or zirconium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof;
each $R^1$ and $R^3$ are, independently, a $C_1$ to $C_8$ alkyl group; and each $R^2$, $R^4$, $R^5$, $R^6$, $R^7$, $R^8$, $R^9$, $R^{10}$, $R^{11}$, $R^{12}$, $R^{13}$, and $R^{14}$ are, independently, hydrogen, or a substituted or unsubstituted hydrocarbyl group having from 1 to 8 carbon atoms, provided however that at least three of the $R^{10}$-$R^{14}$ groups are not hydrogen; and
2) obtaining vinyl terminated polymer having an Mn of 300 g/mol or more and at least 30% allyl chain ends (relative to total unsaturation), as described in co-pending U.S. Ser. No. 13/072,279, filed Mar. 25, 2011, which is incorporated by reference in its entirety herein.

In an embodiment, the polyolefin chain is derived from a higher olefin copolymer comprising allyl chain ends. In an embodiment, the higher olefin copolymer comprising allyl chain ends has an Mn of 300 g/mol or more (measured by $^1$H NMR) comprising:

(i) from about 20 to about 99.9 mol % of at least one $C_5$ to $C_{40}$ higher olefin; and
(ii) from about 0.1 mol % to about 80 mol % of propylene;
wherein the higher olefin copolymer has at least 40% allyl chain ends, as described in U.S. Ser. No. 13/072,249, filed Mar. 25, 2011, which is incorporated by reference in its entirety herein.

In an embodiment, the polyolefin chain is derived from a vinyl terminated branched polyolefin. In an embodiment, the vinyl terminated branched polyolefin has an Mn ($^1$H NMR) of 7,500 to 60,000 g/mol, comprising one or more alpha olefin derived units comprising ethylene and/or propylene, and having;

(i) 50% or greater allyl chain ends, relative to total number of unsaturated chain ends; and
(ii) a g'$_{vis}$ of 0.90 or less, as described in U.S. Ser. No. 61/467,681, filed Mar. 25, 2011, which is incorporated by reference in its entirety herein.

In an embodiment, the polyolefin chain is derived from a vinyl terminated branched polyolefin produced by a process for polymerization, comprising:

(i) contacting, at a temperature greater than 35° C., one or more monomers comprising ethylene and/or propylene, with a catalyst system comprising a metallocene catalyst compound and an activator, wherein the metallocene catalyst compound is represented by the following formula:

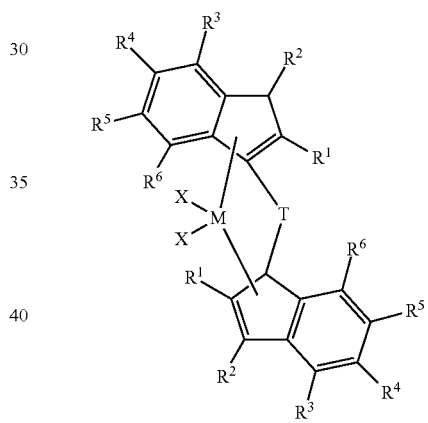

where: M is selected from the group consisting of zirconium or hafnium;
each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system);
each $R^1$, $R^2$, $R^3$, $R^4$, $R^5$, and $R^6$, is, independently, hydrogen or a substituted or unsubstituted hydrocarbyl group, a heteroatom or heteroatom containing group;
further provided that any two adjacent R groups may form a fused ring or multicenter fused ring system where the rings may be aromatic, partially saturated or saturated;
further provided that any of adjacent $R^4$, $R^5$, and $R^6$ groups may form a fused ring or multicenter fused ring system where the rings may be aromatic, partially saturated or saturated;
T is a bridging group represented by the formula (Ra)$_2$J, where J is one or more of C, Si, Ge, N or P, and each Ra is, independently, hydrogen, halogen, $C_1$ to $C_{20}$ hydrocarbyl or a $C_1$ to $C_{20}$ substituted hydrocarbyl, provided that at least one $R^3$ is a substituted or unsubstituted phenyl group, if any of $R^1$, $R^2$, $R^4$, $R^5$, or $R^6$ are not hydrogen;

(ii) converting at least 50 mol % of the monomer to polyolefin; and (iii) obtaining a branched polyolefin having greater than 50% allyl chain ends, relative to total unsaturated chain ends and a Tm of 60° C. or more, as described in U.S. Ser. No. 61/467,681, filed Mar. 25, 2011, which is incorporated by reference in its entirety herein.

In an embodiment, the polyolefin according to structure (I) includes a polyolefin chain ($R^1$) as described herein, and a pyridazine ring of structure (I) wherein $R^2$ and $R^3$ of the pyridazine moiety are independently H or substituted with one or more functional groups. The functional groups may be the same or different on a particular pyridazine ring.

In an embodiment, the polyolefin according to structure (I) includes $R^2$ and $R^3$ of the pyridazine moiety which are each H or a functional group comprising one or more hydrocarbyl group(s), one or more substituted hydrocarbyl group(s), or a combination thereof. In an embodiment, the polyolefin according to structure (I) includes $R^2$ and $R^3$ of the pyridazine moiety which are each H or a functional group comprising from 1 to 20 carbon atoms, nitrogen, oxygen, sulfur, phosphorous, or a combination thereof. In an embodiment, the polyolefin according to structure (I) includes $R^2$ and $R^3$ of the pyridazine moiety which are independently H, comprise one or more functional groups comprising atoms from Groups 13, 14, 15, 16, and 17 of the Periodic Table of Elements, or a combination thereof.

In an embodiment, at least one of $R^2$ and $R^3$ comprise H or a functional group selected from the group consisting of: $C_{1-20}$ linear alkyl, $C_{1-20}$ branched alkyl, $C_{1-20}$ cyclic alkyl, $C_{6-20}$ aromatic, $C_{7-20}$ alkyl-substituted aromatic, $C_{7-20}$ aryl-substituted alkyl, halogenated $C_{1-20}$ alkyl, $C_{1-20}$ alkyloxy, $C_{1-20}$ alkenyloxy, $C_{7-20}$ aryloxy, $C_{7-20}$ cycloalkyloxy, $C_{4-20}$ dienes, alkanol, alkanolamine, acetyl, acetamido, acetoacetyl, acetonyl, acetonylidene, acrylyl, alanyl, allophanoyl, anisyl, acetimido, amidino, amido, amino, aniline, anilino, arsino, azido, azino, azo, azoxy, benzamido, butryl, benzylidine, benzidyne, biphenyl), butylene, iso-butylene, sec-butylene, tert-butylene, carbonyl, carboxy, carbazoyl, caproyl, capryl, carbamido, carbamoyl, carbamyl, carbazoyl, chromyl, cinnamoyl, crotoxyl, cyanato, cyano, cyanamido, decanoly, disiloxanoxy, diazo, diazoamino, disilanyl, epoxy, ethenyl, ethynyl, formamido, formyl, furyl, furfuryl, furfurylideneyl, glutaryl, glycinamido, glycolyl, glycyl, glyocylyl, glycidyl, guanidino, guanyl, halo, hydroxyl, heptadecanoyl, heptanolyl, hydroperoxy, hydroxamino, hydroxylamido, hydrazido, heptanamido, hydrazino, hydrazo, hypophosphito, iodoso, isocyanato, isonitroso, imido, keto, lactyl, methacrylyl, malonyl, methylene, mercapto, methylenyl, nitroamino, nitro, nitrosamino, nitrosimino, nitrosylnitroso, nitrilo, naphthal, naphthobenzyl, naphthyl, naphthylidene, oxy, oxamido, peroxy, phosphinyl, phosphido, phosphito, phospho, phosphono, phosphoryl, isopropylidene, propylenyl, propylidenyl, pryidyl, pyrryl, phenethyl, phenylene, pyridino, phosphinyl, selenyl, seleninyl, selenonyl, siloxy, succinamyl, sulfamino, sulfamyl, sulfeno, silyl, silylenyl, sulfinyl, sulfo, sulfonyl, thiocarboxyl, toluoyl, thenyl, thienyl, thiobenzyl, thiocarbamyl, thiocarbonyl, thiocyanato, thionyl, thiuram, toluidino, tolyl, tolylenyl, tosyl, triazano, trihydrocarbylamino, trihaloamino, trihydrocarbyl trimethylene, trityl, tetrazinyl, ureayl, ureido, valeryl, vinylidenyl, xenyl, xylidino, xylyl, xylylenyl, and combinations thereof.

In an embodiment, at least one of $R^2$ and $R^3$ of the pyridazine moiety comprise a substituted or unsubstituted pyridyl functional group. In an embodiment, a polyolefin comprises one or more pyridazine moieties according to the following formulae:

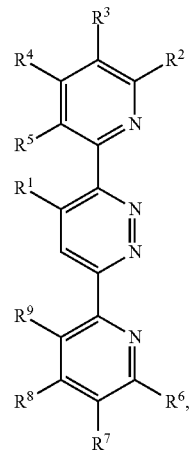

(V)

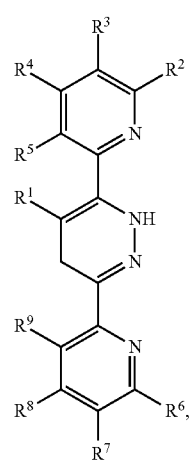

(VI)

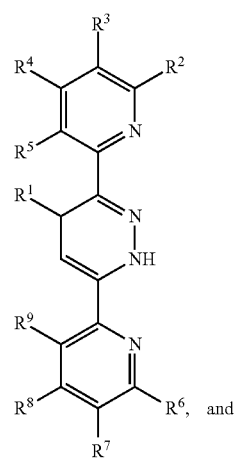

(VII)

and

-continued

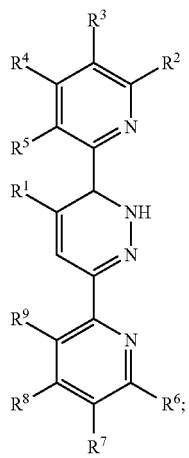

(VIII)

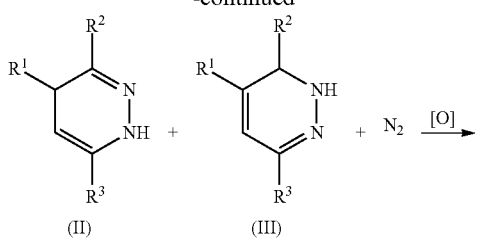

wherein $R^1$ comprises a polyolefin chain attached to the pyridazine moiety through an aliphatic linkage, and wherein $R^2$-$R^9$ ($R^2$, $R^3$, $R^4$, $R^5$, $R^6$, $R^7$, $R^8$, and $R^9$) each independently comprise H, one or more functional groups comprising atoms from Groups 13, 14, 15, 16, and 17 of the Periodic Table of Elements, or a combination thereof.

In an embodiment, a polyolefin comprises a pyridazine moiety attached to the backbone of a polymeric chain, wherein the pyridazine moiety is the cyclo-addition reaction product of a non-aromatic carbon-carbon double bond attached to a backbone of the polyolefin chain through a direct or an aliphatic linkage, and a substituted or unsubstituted tetrazine.

In an embodiment, the polyolefin is the reaction product between a tetrazine and an olefinic moiety attached to the polymer chain. Without wishing to be bound by theory, the inventors surmise that the vinyl terminated polyolefins act as electron rich olefins for an inverse electron demand Diels-Alder reaction. In particular, vinyl terminated polyolefins attached to a backbone of the polyolefin chain through an aliphatic linkage (and not through an aromatic linkage) are particularly useful. Additionally, the inventors have surprisingly found that the methods of the present invention have rates of reaction that are comparable to that of small alkenes. This is unexpected due to the disparity in size, architecture, sterics, and electronics of polymers compared to simple alkenes.

Accordingly, in an embodiment, the pyridazine moiety of the polyolefin (I), (II), (III), and/or (IV) is the cyclo-addition reaction product of a non-aromatic carbon-carbon double bond attached to a backbone of the polyolefin chain ($R^1$) through an aliphatic linkage (IX), and a substituted or unsubstituted tetrazine (X) according to the following reaction:

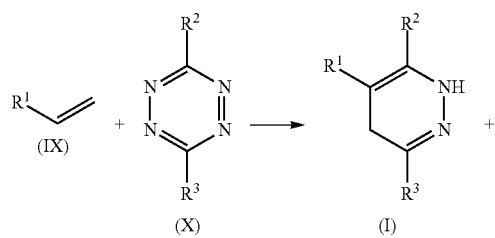

wherein $R^1$ comprises a polyolefin chain attached to the pyridazine moiety through an aliphatic linkage, and wherein $R^2$ and $R^3$ each independently comprise H or one or more functional groups as described herein, comprising atoms from Groups 13, 14, 15, 16, and 17 of the Periodic Table of Elements, or a combination thereof. Without wishing to be bound by theory, the inventors theorize that polyolefins (I), (II), and (III) have pyridazine moieties that are tautomers of each other. Under oxidative conditions, any of these tautomers may rearrange to produce the polyolefin (IV) in one embodiment; however, the inventive nature of the instant disclosure is not dependent on the particular path by which any of the polyolefins is produced. In embodiments herein, the conversion of the polyolefins (I), (II), and/or (III) to the polyolefin (IV) is attenuated by the presence of an oxidizing agent, represented in the reaction above as [O]. Any suitable oxidizing agent may be used. Preferably, the oxidizing agent is one or more of atmospheric oxygen, nitric acid, sulfuric acid, chromic acid, acetic acid, potassium chromate hydrate, and so on. Additional information on the oxidation of the dihydropyridazine ring may be found in U.S. Pat. No. 3,022,305.

In an embodiment, the tetrazine is substituted at $R^2$, $R^3$, or a combination thereof, with a functional group as described herein above. In some embodiments, useful tetrazines include 3,6-diphenyl-1,2,4,5-tetrazine, 3,6-di-2-pyridyl-1,2,4,5-tetrazine, 3,6-bis(2-chlorophenyl)-1,2,4,5-tetrazine, 3-(2-chlorophenyl)-6-(2,6-difluorophenyl)-1,2,4,5-tetrazine, and the like. In an embodiment, the pyridazine moiety of the polyolefins (XIII), (XIV), (XV), and (XVI) are the cyclo-addition reaction product of a vinyl terminated polyolefin (XI) and a di-pyridyl substituted tetrazine (XII) according to the following reaction:

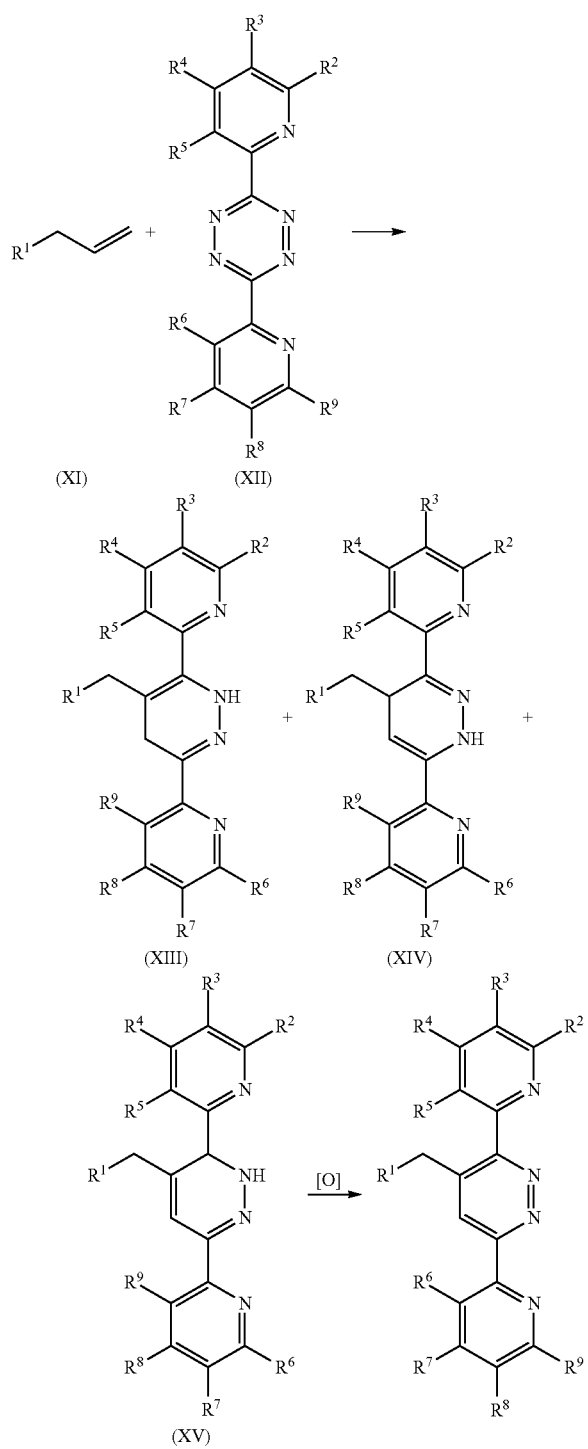

(XI)   (XII)

(XIII)   (XIV)

(XV)

wherein $R^1$ comprises a polyolefin chain attached to the pyridazine moiety through an aliphatic linkage, and wherein $R^2$-$R^9$ ($R^2$, $R^3$, $R^4$, $R^5$, $R^6$, $R^7$, $R^8$, and $R^9$) each independently comprise H or one or more functional groups comprising atoms from Groups 13, 14, 15, 16, and 17 of the Periodic Table of Elements, or a combination thereof. Without wishing to be bound by theory, the inventors theorize that polyolefins (XIII), (XIV) and (XV) have pyridazine moieties that are tautomers of each other. Under oxidative conditions, any of these tautomers may rearrange to produce the polyolefin (XVI) in one embodiment; however, the inventive nature of the instant disclosure is not dependent on the particular path by which any of the polyolefins is produced. In embodiments herein, the conversion of the polyolefins (XIII), (XIV), and/or (XV) to the polyolefin (XVI) is attenuated by the presence of an oxidizing agent, represented in the reaction above as [O]. Any suitable oxidizing agent may be used. Preferably, the oxidizing agent is one or more of atmospheric oxygen, nitric acid, sulfuric acid, chromic acid, acetic acid, potassium chromate hydrate, and so on. Additional information on the oxidation of the dihydropyridazine ring may be found in U.S. Pat. No. 3,022,305. In an embodiment, the tetrazine (XII) contacted with the vinyl terminated polyolefin is 3,6-di-2-pyridyl-1,2,4,5-tetrazine ($R^2$-$R^9$=H).

In any embodiment, the $R^2$ and $R^3$ functional groups can be further reacted to produce other functional groups to further modify the polyolefin for a particular end use.

Compositions

Some embodiments herein relate to a composition comprising: (a) at least one functionalized polymer comprising one or more pyridazine moieties according to the following formulae:

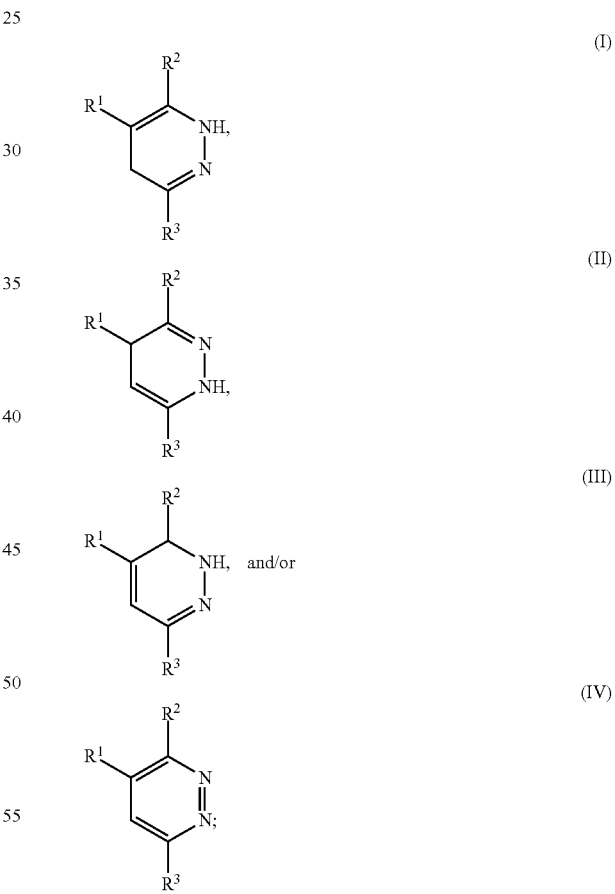

wherein $R^1$ comprises a polyolefin chain attached to the pyridazine moiety through an aliphatic linkage; and
wherein $R^2$ and $R^3$ each comprise H or one or more functional groups comprising atoms from Groups 13, 14, 15, 16, and 17 of the Periodic Table of Elements, or a combination thereof.

In an embodiment, a polyolefin of the present disclosure functionalized with an amine, or an aromatic amine, or pyridines, may be further reacted with an acid and then with a clay to produce a polymer modified clay. In a particular embodiment, a polyolefin functionalized according to the present disclosure with an amine, an aromatic amine, or a pyridine is acidified to produce cationic amine functional groups which can displace sodium ions or other ions found in a clay.

In some embodiments, the composition further comprises at least one phr of a nanoclay. The amount of clay or exfoliated clay incorporated in the polymer-clay composition is generally that which is sufficient to develop an improvement in the mechanical properties or barrier properties of the composition, for example, tensile strength or gas permeability. Amounts generally will be in the range of 0.5 to 10 wt % in one embodiment, and in the range of 1 to 5 wt % in another embodiment, based on the polymer content of the composition. Expressed in parts per hundred rubber, the clay or exfoliated clay may be present in amounts greater than 1 phr, preferably in the range of 1 to 30 phr in one embodiment, and in the range of 5 to 20 phr in another embodiment. As used in the descriptions of the compositions herein, the term "rubber" includes the functionalized polymer of the present invention.

In such embodiments, a layered clay is incorporated into the polyolefins disclosed herein. Individual clay platelet thicknesses are usually about one nanometer, earning them the title of "nanoclays", but surface dimensions are generally 70 to more than 600 nanometers, resulting in an unusually high aspect ratio. This is in distinction to a fine grain carbon black that might have a very small maximum dimension but which has a low ratio of surface area to volume per grain. This high aspect ratio provides the nanoclay with a sheet-like structure. Such materials are typically agglomerated, resulting in a layered clay.

The nanoclay preferably belongs to the general class of clay minerals with expanding crystal lattices commonly referred to as a "smectite" or "smectite-type clay." By way of example, this may include the dioctahedral smectites which consist of montmorillonite, beidellite, and nontronite, and the trioctahedral smectites, which includes saponite, hectorite, and sauconite. Also contemplated are synthetically prepared smectite-clays. In yet other embodiments, the nanoclay is selected from montmorillonite, nontronite, beidellite, bentonite, volkonskoite, laponite, hectorite, saponite, sauconite, magadite, kenyaite, stevensite, vermiculite, halloysite, aluminate oxides, hydrotalcite, and mixtures thereof. Some organoclays are available commercially under the trade designation CLOISITE (available from Southern Clay Products, Gonzalez, Tex.), for example.

These layered clays generally comprise particles containing a plurality of silicate platelets having a thickness of 8 Å-12 Å tightly bound together at interlayer spacings of 4 Å or less, and contain exchangeable cations such as $Na^+$, $Ca^{2+}$, $K+$, or $Mg^{2+}$ present at the interlayer surfaces.

In an embodiment, the layered clay can be exfoliated by suspending the clay in a water solution. In an embodiment, the concentration of clay in water is sufficiently low to minimize the interaction between clay particles and to fully exfoliate the clay. The layered clays described above may also be modified by intercalation or exfoliation by at least one agent, additive, or surfactant capable of undergoing ion exchange reactions with the anions present at the interlayer surfaces of the layered filler to render the clay more hydrophobic. The agents, additives, or surfactants are selected for their capability of undergoing ion exchange reactions with the anions present at the interlayer surfaces of the layered filler. Suitable compounds are cationic surfactants, preferably quaternary ammonium, in which at least two higher molecular weight group and up to two lower molecular weight groups are linked to the nitrogen.

Suitable quaternary ammoniums include, but are not limited to, benzyl trialkyl ammonium, methyl benzyl dialkyl ammonium, methyl benzyl di-hydrogenated tallow ammonium, dimethyl benzyl hydrogenated tallow ammonium, dimethyl ditallow, and dibenzyl dialkyl ammonium.

Examples of suitable modifying additives include cationic surfactants such as ammonium, alkylamines or alkylammonium (primary, secondary, tertiary and quaternary), phosphonium or sulfonium derivatives of aliphatic, aromatic or arylaliphatic amines, phosphines and sulfides. For example, amine compounds (or the corresponding ammonium ion) are those with the structure $R^2R^3R^4N$, wherein $R^2$, $R^3$, and $R^4$ are $C_1$ to $C_{30}$ alkyls or $C_2$ to $C_{30}$ alkenes in one embodiment, $C_1$ to $C_{20}$ alkyls or $C_2$ to $C_{20}$ alkenes in another embodiment, which may be the same or different. In one embodiment, the exfoliating additive is a long chain tertiary amine, wherein at least $R^2$ is a $C_{14}$ to $C_{20}$ alkyl or alkene.

In particular embodiments, the layered clays may contain a benzyl functionality which provides for improvement in the separation of the clay layers in the polymer, thereby improving the impermeability of the elastomeric nanocomposite, as described in U.S. application Ser. No. 12/851,264. Thus one of the lower molecular weight groups linked to the quaternary ammonium is a benzyl derived unit. The ammonium may be structurally described as follows:

$$(R^5R^6R^7R^8)N^+$$

wherein $R^5$ is benzyl derived unit, which may or may not be substituted, wherein $R^6$ is selected from $C_1$ to $C_{26}$ alkyls, $C_2$ to $C_{26}$ alkenes, and $C_3$ to $C_{26}$ aryls, and wherein $R^7$ and $R^8$ are the same or different and are independently selected from $C_9$ to $C_{26}$ alkyls, $C_9$ to $C_{26}$ alkenes, and $C_9$ to $C_{26}$ aryls.

In other embodiments, a class of exfoliating additives includes those which can covalently bond to the interlayer surfaces. These include polysilanes of the structure $—Si(R^9)_2 R^{10}$ where $R^9$ is the same or different at each occurrence and is selected from alkyl, alkoxy or oxysilane and $R^{10}$ is an organic radical compatible with the matrix polymer of the composite. Other suitable exfoliating additives include protonated amino acids and salts thereof containing 2-30 carbon atoms such as 12-aminododecanoic acid, epsilon-caprolactam and like materials.

In an embodiment, nanoclay nanocomposites can generally be prepared using a variety of processes, such as solution blending, melt blending, or an emulsion process. As used herein, fillers can include inorganic particles forming part of the nanocomposite matrix, e.g., clay particles having a dimension in the nanometer range, and larger clay particles can also be used as an additional filler in the nanocomposites, if desired.

In one embodiment, an organoclay is formed, e.g., in situ, as the reaction product of the layered clay and the polyolefin functionalized with an amine, or an aromatic amine, or pyridines, and acidified as described above. In an embodiment, the modified polyolefin comprising pyridyl functional groups may be contacted with an acid at a temperature and for a period of time sufficient to produce a polyolefin comprising a pyridyl salt, which may be subsequently contacted with a clay or other substrate at a temperature and for a period of time sufficient to produce a polymer modified clay comprising the functionalized polyolefin bonded to the clay. In one embodiment, the nanoclay composite is prepared in situ by using melt mixing the vinyl-terminated polyolefin, the pyridyl-substituted tetrazine, acid and clay, e.g., in a click chemistry system. In an embodiment, the clay comprises nanometer scale particles or larger.

In an embodiment, the polymer modified clay is produced in a melt under agitation (e.g., in a BRABENDER mixer or the like) by sequential addition of the vinyl terminated polymer and the substituted tetrazine for a period of time and at a temperature sufficient to produce the polymer, followed by addition of an acid (e.g., p-toluene (para-toluene) sulfonic acid or the like) with mixing for a period of time and at a temperature sufficient to produce a salt from the pyridine moieties, followed by addition of a clay and optionally one or more base resins to produce a polymer modified clay. In an embodiment, the various components may be added individually, simultaneously, or any combination thereof.

In an embodiment, polymer modification of other materials suitable for composites having nanometer scale particles or larger may be conducted as described for clay. Such materials suitable for composites include, but are not limited to, graphene, carbon nanotubes, graphite, metallic fillers such as iron, ferrous hydroxide, ferric/ferrous oxides, silver, other metal oxides, and the like.

In an embodiment, the tetrazine comprises pyridyl or other amine functional groups suitable to form complexes with various metals. In an embodiment, $R^1$ may be an ethylene-diene copolymer, which may include ethylene-norbornene copolymers and the like, to produce modified polyolefins suitable to form a complex with one or more metals to produce a functionalized polymer suitable for use as coating, anti-fouling coating, metal composite, metal complex, or the like. In an embodiment, a polyolefin functionalized with an amine, or an aromatic amine, or pyridines may be further used to treat metal surfaces by contacting a metal surface with a functionalized polyolefin under conditions sufficient to produce co-ordinate bonds between the metal surface and the functional groups, to produce a monolayer, one or more layers of a bi-layer, or other type of film of the functionalized polyolefin on the metal surface.

In an embodiment, a functionalized polyolefin may be complexed with metal atoms such as Cu, Ag, Fe, and the like to produce supramolecular chemical structures.

In an embodiment, the functionalized polyolefins may be combined with conventional additives known in the art, including fillers, antioxidants, adjuvants, adhesion promoters, plasticizers, oils, low molecular weight polymers, block, antiblock, pigments, processing aids, UV stabilizers, neutralizers, surfactants nucleating agents, oxidized polyolefins, acid modified polyolefins, and/or anhydride modified polyolefins. Additives are combined with polymer compositions as individual components, in masterbatches, or combinations thereof.

Fillers include conventional fillers known to those skilled in the art, including titanium dioxide, calcium carbonate, mica, zinc oxides, starch, barium sulfate, silica, silicon dioxide, carbon black, sand, glass beads, mineral aggregates, talc, and/or clay.

Antioxidants include conventional antioxidants known to those skilled in the art, including phenolic antioxidants, such as IRGANOX 1010 and IRGANOX 1076 both available from Ciba-Geigy (now available from BASF, Florham Park, N.J.). In some embodiments, adhesive compositions include less than about 3 wt % antioxidant.

Oils include conventional oils known to those skilled in the art, including paraffinic or naphthenic oils such as PRIMOL 352 and PRIMOL 876 available from ExxonMobil Chemical France, S.A. in Paris, France.

Plasticizers include conventional plasticizers known to those skilled in the art, including mineral oils, phthalates, or polybutenes, such as PARAPOL 950 and PARAPOL 1300 formerly available from ExxonMobil Chemical Company in Houston, Tex. Some representative plasticizers include phthalates such as di-iso-undecyl phthalate (DIUP), di-iso-nonylphthalate (DINP), and dioctylphthalates (DOP).

Adhesion promoters include conventional adhesion promoters known to those skilled in the art. Adhesion promoters include polar acids; polyaminoamides, such as VERSAMID 115, 125, 140, available from Cognis Ltd. (Osaka, Japan); urethanes, such as isocyanate/hydroxy terminated polyester systems, e.g., bonding agent TN/MONDUR CB-75 (Mobay Chemical Corporation, now Bayer Corporation, Pittsburgh, Pa.), coupling agents, such as silane esters such as Z-6020 which is commercially available from Dow Corning (Midland, Mich.); titanate esters, such as KR-44 commercially available from Kenrich Petrochemicals (Bayonne, N.J.); reactive acrylate monomers, such as SARBOX SB-600 from Sartomer USA, LLC (Exton, Pa.); metal acid salts, such as SARET 633 from Sartomer USA; and polyphenylene oxide.

Embodiments of the present disclosure may find utility in nanocomposites, coating applications (including anti-fouling coatings), metal composites, metal complexes, dispersant applications, and as viscosity index improvers, or multifunctional viscosity index improvers. Additionally they may be used as disinfectants (functionalized amines) and or wetting agents.

Functionalized polyolefins of the present invention having uses as dispersants typically have Mns (g/mol) of less than 20,000, preferably less than 10,000 and most preferably less than 8,000 and typically can range from 500 to 10,000 (e.g., 500 to 5,000), preferably from 1,000 to 8,000 (e.g., 1,000 to 5,000) and most preferably from 1,500 to 6,000 (e.g., 1,500 to 3,000). For more information on dispersants, generally, see U.S. Pat. No. 5,616,153.

The functionalized polyolefins described herein having Mns (g/mol) of greater than 10,000 (preferably greater than 10,000 to 30,000; preferably 20,000 to 30,000) are useful for viscosity index improvers for adhesive additives, antifogging and wetting agents, ink and paint adhesion promoters, coatings, tackifiers and sealants, and the like. In addition, such polyolefins may be functionalized and derivatized to make multifunctional viscosity index improvers which also possess dispersant properties.

The invention, accordingly, provides the following embodiments:

1. A polyolefin comprising one or more pyridazine moieties according to the following formulae:

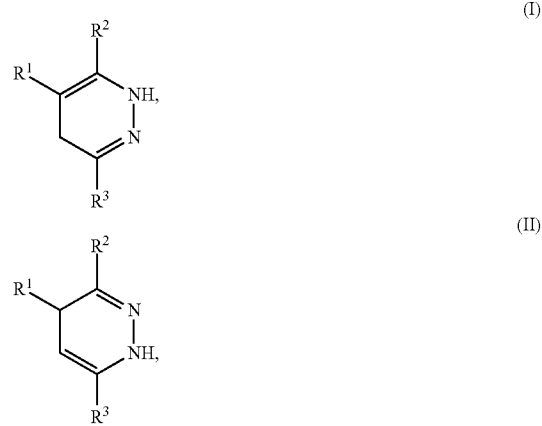

-continued

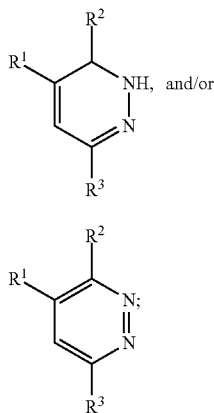

wherein R¹ comprises a polyolefin chain attached to the pyridazine moiety (preferably the pyridazine moiety is a terminal moiety of the polyolefin chain) through an aliphatic linkage; and wherein R² and R³ each comprise H or one or more functional groups comprising atoms from Groups 13, 14, 15, 16, and 17 of the Periodic Table of Elements, or a combination thereof (preferably at least one of R² and R³ comprises from 1 to 20 carbon atoms, nitrogen, oxygen, sulfur, phosphorous, or a combination thereof; preferably at least one of R² and R³ comprise a functional group selected from the group consisting of:

$C_{1-20}$ linear alkyl, $C_{1-20}$ branched alkyl, $C_{1-20}$ cyclic alkyl, $C_{6-20}$ aromatic, $C_{7-20}$ alkyl-substituted aromatic, $C_{7-20}$ aryl-substituted alkyl, halogenated $C_{1-20}$ alkyl, $C_{1-20}$ alkyloxy, $C_{1-20}$ alkenyloxy, $C_{7-20}$ aryloxy, $C_{7-20}$ cycloalkyloxy, $C_{4-20}$ dienes, alkanol, alkanolamine, acetyl, acetamido, acetoacetyl, acetonyl, acetonylidene, acrylyl, alanyl, allophanoyl, anisyl, acetimido, amidino, amido, amino, aniline, anilino, arsino, azido, azino, azo, azoxy, benzamido, butryl, benzylidine, benzidyne, biphenyl), butylene, iso-butylene, sec-butylene, tert-butylene, carbonyl, carboxy, carbazoyl, caproyl, capryl, carbamido, carbamoyl, carbamyl, carbazoyl, chromyl, cinnamoyl, crotoxyl, cyanato, cyano, cyanamido, decanoly, disiloxanoxy, diazo, diazoamino, disilanyl, epoxy, ethenyl, ethynyl, formamido, formyl, furyl, furfuryl, furfurylideneyl, glutaryl, glycinamido, glycolyl, glycyl, glyocylyl, glycidyl, guanidino, guanyl, halo, hydroxyl, heptadecanoyl, heptanolyl, hydroperoxy, hydroxamino, hydroxylamido, hydrazido, heptanamido, hydrazino, hydrazo, hypophosphito, iodoso, isocyanato, isonitroso, imido, keto, lactyl, methacrylyl, malonyl, methylene, mercapto, methylenyl, nitroamino, nitro, nitrosamino, nitrosimino, nitrosylnitroso, nitrilo, naphthal, naphthobenzyl, naphthyl, naphthylidene, oxy, oxamido, peroxy, phosphinyl, phosphido, phosphito, phospho, phosphono, phosphoryl, isopropylidene, propylenyl, propylidenyl, pryidyl, pyrryl, phenethyl, phenylene, pyridino, phosphinyl, selenyl, seleninyl, selenonyl, siloxy, succinamyl, sulfamino, sulfamyl, sulfeno, silyl, silylenyl, sulfinyl, sulfo, sulfonyl, thiocarboxyl, toluoyl, thenyl, thienyl, thiobenzyl, thiocarbamyl, thiocarbonyl, thiocyanato, thionyl, thiuram, toluidino, tolyl, tolylenyl, tosyl, triazano, trihydrocarbylamino, trihaloamino, trihydrocarbyl trimethylene, trityl, tetrazinyl, ureayl, ureido, valeryl, vinylidenyl, xenyl, xylidino, xylyl, xylylenyl, and combinations thereof; preferably at least one of R² and R³ comprise a pyridyl functional group).

2. The polyolefin of claim 1, wherein R¹ comprises a $C_{2-20}$ poly-alpha-olefin having a weight average molecular weight of greater than or equal to about 2,500 g/mol (preferably R¹ is derived from polyethylene, polypropylene, polybutadiene, butyl rubber, or a combination thereof) or, R¹ is derived from one or more of:
(i) a vinyl terminated polymer having at least 5% allyl chain ends;
(ii) a vinyl terminated polymer having an Mn of at least 200 g/mol (measured by ¹H NMR) comprising of one or more $C_4$ to $C_{40}$ higher olefin derived units, where the higher olefin polymer comprises substantially no propylene derived units; and wherein the higher olefin polymer has at least 5% allyl chain ends;
(iii) a copolymer having an Mn of 300 g/mol or more (measured by ¹H NMR) comprising (a) from about 20 mol % to about 99.9 mol % of at least one $C_5$ to $C_{40}$ higher olefin, and (b) from about 0.1 mol % to about 80 mol % of propylene, wherein the higher olefin copolymer has at least 40% allyl chain ends;
(iv) a copolymer having an Mn of 300 g/mol or more (measured by ¹H NMR), and comprises (a) from about 80 mol % to about 99.9 mol % of at least one $C_4$ olefin, (b) from about 0.1 mol % to about 20 mol % of propylene; and wherein the vinyl terminated macromonomer has at least 40% allyl chain ends relative to total unsaturation;
(v) a co-oligomer having an Mn of 300 g/mol to 30,000 g/mol (measured by ¹H NMR) comprising 10 mol % to 90 mol % propylene and 10 mol % to 90 mol % of ethylene, wherein the oligomer has at least X % allyl chain ends (relative to total unsaturations), where: 1) X=(−0.94*(mol % ethylene incorporated)+100), when 10 mol % to 60 mol % ethylene is present in the co-oligomer, 2) X=45, when greater than 60 mol % and less than 70 mol % ethylene is present in the co-oligomer, and 3) X=(1.83*(mol % ethylene incorporated)−83), when 70 mol % to 90 mol % ethylene is present in the co-oligomer;
(vi) a propylene oligomer, comprising more than 90 mol % propylene and less than 10 mol % ethylene wherein the oligomer has: at least 93% allyl chain ends, a number average molecular weight (Mn) of about 500 g/mol to about 20,000 g/mol, an isobutyl chain end to allylic vinyl group ratio of 0.8:1 to 1.35:1.0, and less than 100 ppm aluminum;
(vii) a propylene oligomer, comprising: at least 50 mol % propylene and from 10 mol % to 50 mol % ethylene, wherein the oligomer has: at least 90% allyl chain ends, an Mn of about 150 g/mol to about 10,000 g/mol, and an isobutyl chain end to allylic vinyl group ratio of 0.8:1 to 1.2:1.0, wherein monomers having four or more carbon atoms are present at from 0 mol % to 3 mol %;
(viii) a propylene oligomer, comprising: at least 50 mol % propylene, from 0.1 mol % to 45 mol % ethylene, and from 0.1 mol % to 5 mol % $C_4$ to $C_{12}$ olefin, wherein the oligomer has: at least 90% allyl chain ends, an Mn of about 150 g/mol to about 10,000 g/mol, and an isobutyl chain end to allylic vinyl group ratio of 0.8:1 to 1.35:1.0;
(ix) a propylene oligomer, comprising: at least 50 mol % propylene, from 0.1 mol % to 45 mol % ethylene, and from 0.1 mol % to 5 mol % diene, wherein the oligomer has: at least 90% allyl chain ends, an Mn of about 150 g/mol to about 10,000 g/mol, and an isobutyl chain end to allylic vinyl group ratio of 0.7:1 to 1.35:1.0; and
(x) a homo-oligomer, comprising propylene, wherein the oligomer has: at least 93% allyl chain ends, an Mn of about 500 g/mol to about 20,000 g/mol, an isobutyl chain end to allylic vinyl group ratio of 0.8:1 to 1.2:1.0, and less than 1400 ppm aluminum.

3. The polyolefin of paragraphs 1 and 2, wherein the pyridazine moiety is the cyclo-addition reaction product of a non-aromatic carbon-carbon double bond (preferably a terminal vinyl functional group) attached to a backbone of the polyolefin chain through an aliphatic linkage, and a substituted or unsubstituted tetrazine (preferably the tetrazine is one of 3,6-diphenyl-1,2,4,5-tetrazine, 3,6-di-2-pyridyl-1,2,4,5-tetrazine, 3,6-bis(2-chlorophenyl)-1,2,4,5-tetrazine, 3-(2-chlorophenyl)-6-(2,6-difluorophenyl)-1,2,4,5-tetrazine, and the like).

4. A method to produce the polyolefin of paragraphs 1 to 3 comprising:

contacting a first polyolefin comprising at least one non-aromatic carbon-carbon double bond (preferably the first polyolefin is vinyl terminated) with a substituted or unsubstituted tetrazine (preferably 3,6-diphenyl-1,2,4,5-tetrazine, 3,6-di-2-pyridyl-1,2,4,5-tetrazine, 3,6-bis(2-chlorophenyl)-1,2,4,5-tetrazine, 3-(2-chlorophenyl)-6-(2,6-difluorophenyl)-1,2,4,5-tetrazine, and the like) at a temperature and for a period of time sufficient to produce a second polyolefin comprising one or more pyridazine moieties according to the following formulae:

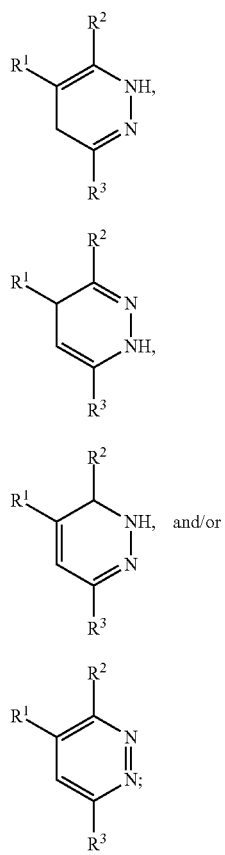

wherein $R^1$ comprises the first polyolefin attached to the pyridazine moiety through an aliphatic linkage, and wherein $R^2$ and $R^3$ each comprise H or one or more functional groups comprising atoms from Groups 13, 14, 15, 16, and 17 of the Periodic Table of Elements, or a combination thereof; optionally contacting the second polyolefin with an acid at a temperature and for a period of time sufficient to produce a third polyolefin comprising a pyridyl salt;

optionally contacting the third polyolefin with a clay at a temperature and for a period of time sufficient to produce a polymer modified clay comprising the third polyolefin bonded to the clay (preferably the clay is a nanoclay; preferably the nanoclay is selected from montmorillonite, nontronite, beidellite, bentonite, volkonskoite, laponite, hectorite, saponite, sauconite, magadite, kenyaite, stevensite, vermiculite, halloysite, aluminate oxides, hydrotalcite, and mixtures thereof).

5. A composition comprising the polyolefin of paragraphs 1 to 3.

6. The composition of paragraph 5, further comprising at least one phr of a nanoclay (preferably the nanoclay is selected from montmorillonite, nontronite, beidellite, bentonite, volkonskoite, laponite, hectorite, saponite, sauconite, magadite, kenyaite, stevensite, vermiculite, halloysite, aluminate oxides, hydrotalcite, and mixtures thereof).

7. The composition of paragraphs 5 and 6, further comprising one or more of fillers, antioxidants, oils, or adhesion promoters.

8. The use of the composition of paragraphs 5 to 7 in nanocomposites, coatings, anti-fouling coatings, metal composites, metal complexes, disinfectants, wetting agents, dispersants, viscosity index improvers or multifunctional viscosity index improvers.

EXAMPLES

Product Characterization
Products were characterized by $^1$H NMR and $^{13}$C NMR as follows:
$^1$H NMR
$^1$H NMR data was collected at either room temperature or 120° C. (for purposes of the claims, 120° C. shall be used) in a 5 mm probe using a spectrometer with a $^1$H frequency of at least 400 MHz. Data was recorded using a maximum pulse width of 45° C., 8 seconds between pulses and signal averaging 120 transients.
$^{13}$C NMR
$^{13}$C NMR data was collected at 120° C. using a spectrometer with a $^{13}$C frequency of at least 100 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating was employed during the entire acquisition period. The spectra were acquired with time averaging to provide a signal to noise level adequate to measure the signals of interest. Samples were dissolved in tetrachloroethane-$d_2$ (TCE) at concentrations between 10 to 15 wt % prior to being inserted into the spectrometer magnet.

Prior to data analysis spectra were referenced by setting the chemical shift of the TCE solvent signal to 74.39 ppm.

Example 1

A vinyl terminated polypropylene oligomer (5.377 grams, 0.84 mmol) having a Mw of 6,400 g/mol and 98 wt % vinyl chain ends (determined by $^1$H NMR) was combined in a glass vial at a 0.5:1 stoichiometric amount with 3,6-di-2-pyridyl-1,2,4,5-tetrazine (0.42 mmol, Mw 236 g/mol, 99.1 mg), which was added as a dry red powder. A magnetic stir bar was added to the vial which was then heated to 170° C. with 500 rpm mixing. Once no observable bubbles could be seen (after about 25 minutes), the sample was cooled to room temperature and observed to be a transparent orange viscous liquid (Sample A).

Example 2

A BRABENDER mixer was preheated to 200° C. for 10 minutes, cooled to 190° C. and to this a mixture of a vinyl terminated polyethylene (PAXON EA55003, ExxonMobil Chemical Corporation, 50 g, Mn 17,000 g/mol, 2.94 mmol, 95%+vinyl chain ends) and 3,6-di-2-pyridyl-1,2,4,5-tetrazine (0.7 g, Mn=236 g/mol, 2.96 mmol) was added. The sample was seen to become a viscous dark red cloudy melt. After 10 minutes, the mixture was seen to have become a translucent orange melt and an additive package of 25 mg IRGANOX 1076, 100 mg IRGAFOS 168 (available from BASF Corporation) and 40 mg DYNAMAR FX5920A (available from Dyneon LLC, Oakdale, Minn.) was added. The reaction mixture was blended for 5 minutes further to produce Sample B.

Example 3 (Comparative)

The comparative sample was produced using the same procedure as in Example 1, but without the tetrazine addition. This sample is a control (Comparative Sample C).

Figure 1B:
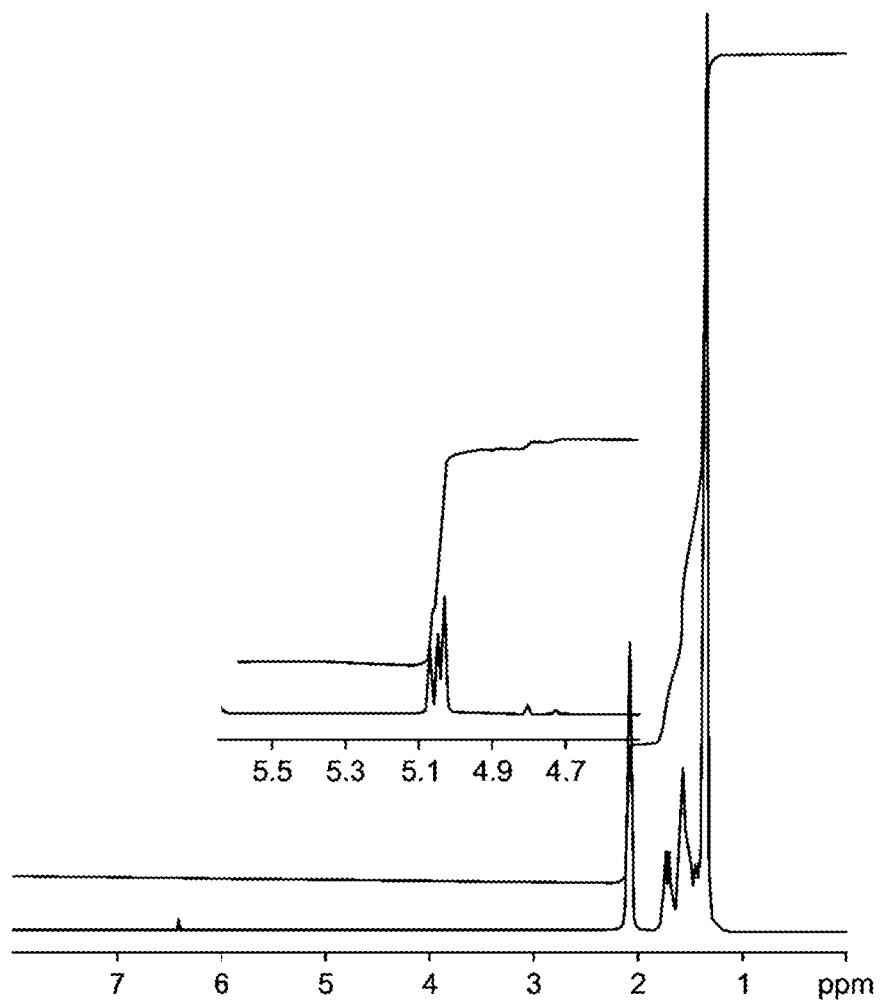
FIG. 1B is a $^1$H NMR spectrum of a functionalized polyolefin according to an embodiment of this invention.
Figure 1C:
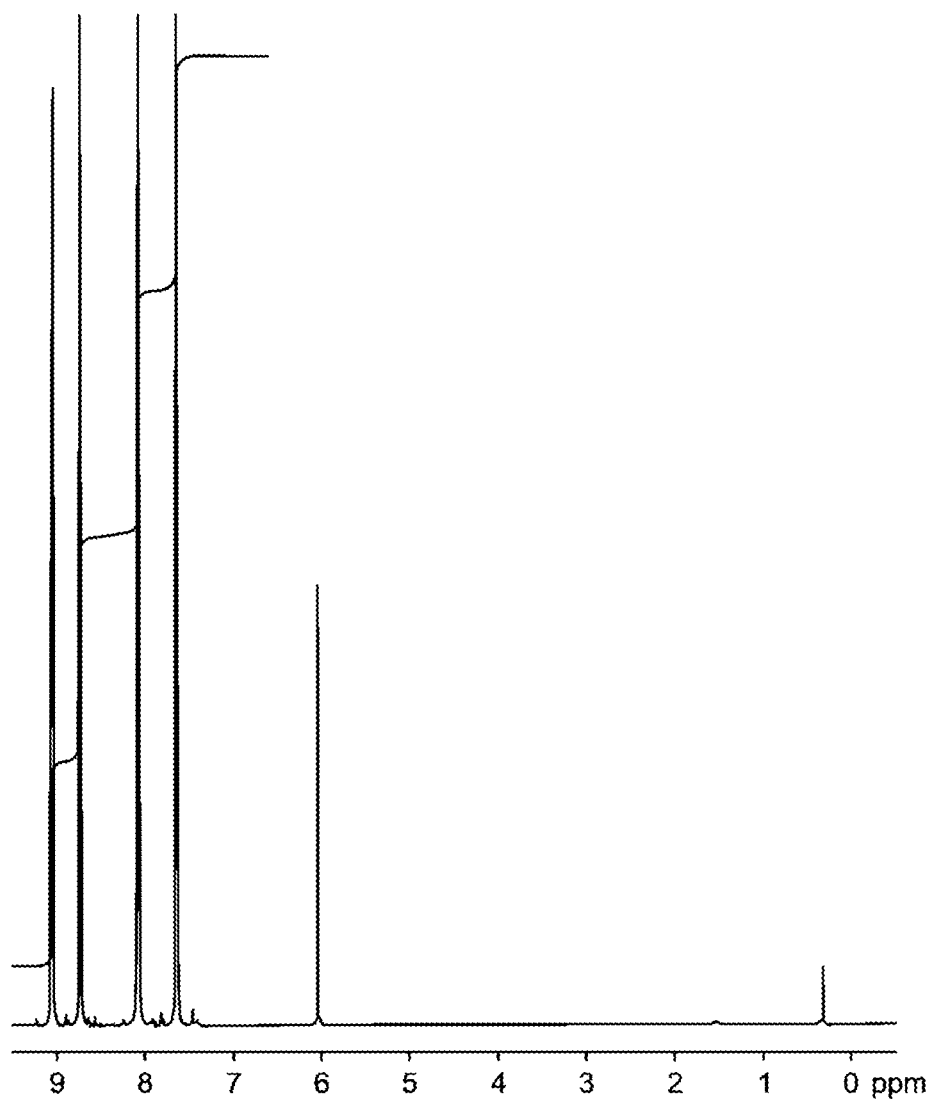
FIG. 1C is a $^1$H NMR spectrum of 3,6-di-2-pyridyl-1,2,4,5-tetrazine in tetrachloroethane.
Figure 1D:
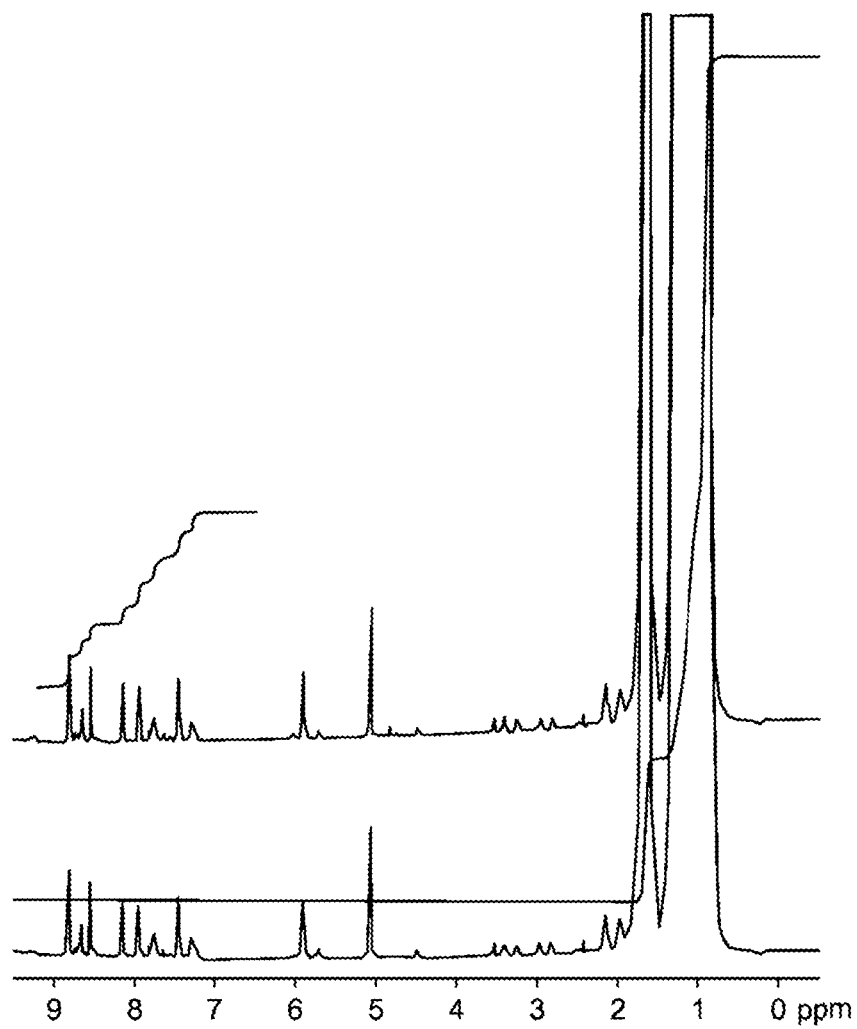
FIG. 1D is a $^1$H NMR spectrum of a functionalized polyolefin according to an embodiment of this invention.

FIG. 1A shows the $^1$H NMR spectrum of the vinyl terminated polypropylene of Example 1, which has a vinyl content of 1.98 carbons/1000 carbons. FIG. 1B shows the $^1$H NMR spectrum of Sample A, which shows a vinyl content of 1.02 carbons/1000 carbons, which indicates 48.5% of the vinyl carbons originally present on the vinyl terminated polypropylene have reacted. This is in accordance with what would be expected for the 0.484:1 stoichiometric ratio used (considering the Aldrich specified 96+% purity). The remaining vinyl groups remain unreacted. FIG. 1C shows the $^1$H NMR spectrum of 3,6-di-2-pyridyl-1,2,4,5-tetrazine in tetrachloroethane. FIG. 1D shows the $^1$H NMR spectrum of Sample A on a magnified scale, which is compared to that of 3,6-di-2-pyridyl-1,2,4,5-tetrazine shown in FIG. 1C. The peaks at 8.99, 8.75, 8.01, and 7.58 have been previously assigned to the (6,6'), (3,3'), (4,4'), and (5,5') protons of the pyridine ring. The 8.99 ppm peak completely disappears in the final polymer and all peaks are seen to have been shifted upfield. The peaks are also seen to be split which is expected once the reaction converting the symmetric tetrazine to an asymmetric pyridazine has happened. The 5 peaks between 7 to 8.2 ppm can be integrated into 5 protons of equal height and the region between 8.4 ppm and 9.0 ppm corresponds to 3 more protons. The 8 protons of the pyridine rings remain intact.

FIG. 2 shows the complex viscosity versus frequency plot of vinyl terminated polyethylene starting material of Example 2, Sample B, and Comparative Sample C. As the data show, no significant change in rheological behavior is seen between the functionalized polymer according to the present disclosure and that of the original polymer. The lack of change of viscosity at similar frequencies between the two samples shows that there was no significant cross linking or chain scission during the reaction of the polyethylene with the tetrazine. Accordingly, the functionalized polymer advantageously retains its rheological behavior.

Figure 3A:
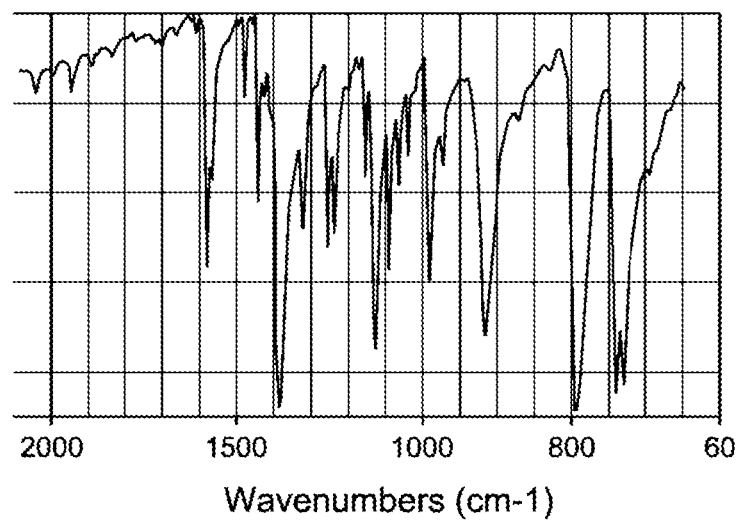
FIG. 3A is a Fourier transform infrared (FTIR) spectrum of 3,6-di-2-pyridyl-1,2,4,5-tetrazine.
Figure 3B:
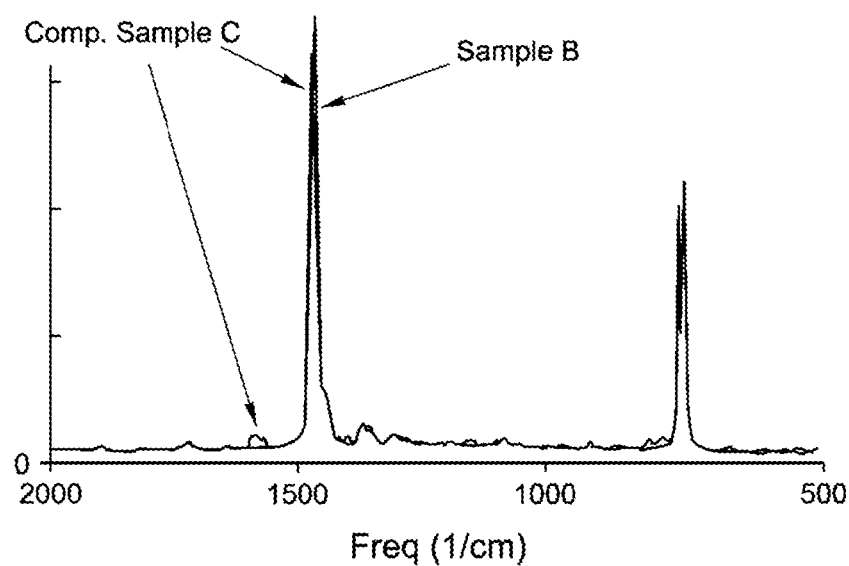
FIG. 3B is a partial FTIR spectrum of a functionalized polyolefin according to an embodiment of this invention and a Comparative Sample.

FIG. 3A shows the FTIR spectrum for 3,6-di-2-pyridyl-1,2,4,5-tetrazine and FIG. 3B shows the FTIR spectrum of Sample B from Example 2 compared to Comparative Sample C. The four peaks visible in the region of 1550-1580 cm$^{-1}$ confirm the C—N groups and these are shifted with respect to the location of the two peaks of base material in the same region.

The analysis using NMR and FTIR gives an indication that the vinyl terminated polyolefins were successfully end functionalized. This functional group is a dipyridyl pyridazine and is weakly basic.

Example 4

In another example, a BRABENDER mixer was heated to 190° C. and to this 50 grams of vinyl terminated polyethylene (PAXON EA55-003, ExxonMobil) granules (95% vinyl terminated, determined by $^1$H NMR) was added with 0.35 grams of bipyridyl tetrazine (3,6-di-2-pyridyl-1,2,4,5-tetrazine, 0.5 mol tetrazine groups per 1 mol vinyl groups). The mixture was mixed at 40 rpm for 10 minutes after which 0.255 grams of dried p-toluene sulphonic acid was added (1 mol acid per 1 mol tetrazine groups). An additive package consisting of IRGANOX 1076 (500 ppm), IRGAFOS 168 (1000 ppm), and DYNAMAR 5920 (800 ppm) was also added at this time. After 5 minutes of additional mixing, 2.5 grams (to obtain 5 wt %) of dried montmorillonite clay was added. The sample was mixed for 5 minutes further and removed from the BRABENDER. The maroon colored sample produced was a functionalized polymer modified clay wherein the functionalized polyolefin was bonded to the clay.

Kinetics Studies

Kinetics Study of the Reaction Between Vinyl Terminated Polypropylene and 3,6-di-2-pyridyl-1,2,4,5-Tetrazine In a 20 ml vial, 1.6 g (1.0 mmol) of atactic polypropylene ($M_n$=1.6 k g/mol, vinyl content=93%) was dissolved in 4 ml of 1,1,2,2-tetrachloroethane-d2 (TCE-d2). 3,6-di-2-pyridyl-1,2,4,5-tetrazine (DPTZ, 0.28 g, 1.2 mmol) was dissolved in 2 ml TCE-d2, and then was transferred to the reaction vial containing atactic polypropylene. The vial was placed onto a preheated hotplate stirrer at 60° C. and an initial sample was taken. Samples were taken at different time intervals during the reaction for $^1$H NMR analysis to monitor the reaction progress. Kinetics studies at 40° C. were carried out in a similar fashion. Table 1 shows the progress of the reaction (%) monitored by vinyl bond conversion.

TABLE 1

Kinetic Data For The Reaction Between Atactic Polypropylene And DPTZ

| Time | Reaction Progress (%) | |
|---|---|---|
| (minutes) | 40° C. | 60° C. |
| 0 | 0% | 10% |
| 10 | 20% | — |
| 30 | 35% | — |
| 60 | 50% | 94% |
| 120 | 61% | 100% |
| 180 | 63% | — |
| 240 | 66% | — |

Kinetics Study of the Reaction Between $C_{10}$ Alkenes and 3,6-di-2-pyridyl-1,2,4,5-Tetrazine The alkenes (1-decene, 2-methyl-1-nonene and 5-decene, 0.11 g (0.8 mmol) each) were dissolved in 6 ml CDCl$_3$. DPTZ (0.56 g, 2.4 mmol) was dissolved into 12 ml CDCl$_3$ and added to the solution of alkenes. The solution was immediately evenly divided into 3 vials which were placed on pre-heated hotplate stirrer at room temperature (22° C.), 40° C. and 60° C. respectively. Initial samples were taken at this time (time 0 minutes), and samples were taken at different intervals during the reaction. $^1$H NMR analysis was used to monitor the reaction progress, and the data is reported in Table 2. All values reported are the mole fractions of double bonds (at original peak location) remaining in the sample. Vinylidene peaks were located at 4.7 ppm, vinyl peaks at 5.0 ppm and vinylene peaks at 5.4 ppm.

TABLE 2

| | Kinetic Data For The Reaction Between $C_{10}$ Alkenes And DPTZ | | | | | | | | |
|---|---|---|---|---|---|---|---|---|---|
| | Temp. | | | | | | | | |
| Time | 22° C. | | | 40° C. | | | 60° C. | | |
| (mins) | Vinylidene | Vinyl | Vinylene | Vinylidene | Vinyl | Vinylene | Vinylidene | Vinyl | Vinylene |
| 0 | 0.33 | 0.33 | 0.33 | 0.33 | 0.33 | 0.33 | 0.33 | 0.33 | 0.33 |
| 10 | 0.32 | 0.34 | 0.34 | 0.36 | 0.30 | 0.34 | 0.38 | 0.24 | 0.37 |
| 20 | 0.34 | 0.34 | 0.32 | 0.37 | 0.27 | 0.36 | 0.40 | 0.19 | 0.40 |
| 30 | 0.35 | 0.32 | 0.33 | 0.38 | 0.25 | 0.37 | 0.42 | 0.15 | 0.43 |
| 60 | 0.36 | 0.27 | 0.37 | 0.42 | 0.18 | 0.40 | 0.48 | 0.06 | 0.46 |
| 90 | 0.37 | 0.22 | 0.41 | — | — | — | 0.51 | 0.00 | 0.49 |
| 120 | 0.38 | 0.21 | 0.40 | 0.45 | 0.09 | 0.46 | — | — | — |
| 180 | 0.42 | 0.15 | 0.43 | — | — | — | 0.51 | 0.00 | 0.49 |
| 240 | 0.44 | 0.12 | 0.44 | 0.50 | 0.00 | 0.50 | 0.54 | 0.00 | 0.46 |

The data shows that the vinyl bond reacts preferentially with the tetrazine. The reactivity of the vinylene and vinylidene are similar to each other and the reaction rate is much slower than the vinyl bond. The data also shows that the reaction rate of the above reaction with atactic polypropylene is surprisingly very similar to that with the small molecule decene (for example, at 60° C. reaction is complete in 90 minutes with decene and 120 minutes with atactic polypropylene).

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A polyolefin comprising one or more pyridazine moieties according to the following formulae:

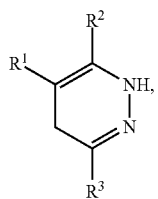

(I)

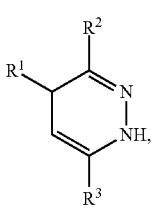

(II)

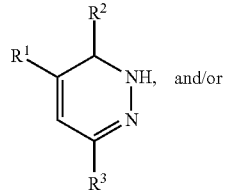

(III)

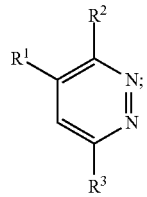

(IV)

wherein $R^1$ comprises a polyolefin chain attached to the pyridazine moiety through an aliphatic linkage; and wherein $R^2$ and $R^3$ each comprise H or one or more functional groups comprising atoms from Groups 13, 14, 15, 16, and 17 of the Periodic Table of Elements, or a combination thereof, and wherein at least one of $R^2$ and $R^3$ comprises from 1 to 20 carbon atoms, nitrogen, oxygen, sulfur, phosphorous, or a combination thereof.

2. The polyolefin of claim 1, wherein the pyridazine moiety is a terminal moiety of the polyolefin chain.

3. The polyolefin of claim 1, wherein at least one of $R^2$ and $R^3$ comprises a functional group selected from the group consisting of: $C_{1-20}$ linear alkyl, $C_{1-20}$ branched alkyl, $C_{1-20}$ cyclic alkyl, $C_{6-20}$ aromatic, $C_{7-20}$ alkyl-substituted aromatic, $C_{7-20}$ aryl-substituted alkyl, halogenated $C_{1-20}$ alkyl, $C_{1-20}$ alkyloxy, $C_{1-20}$ alkenyloxy, $C_{7-20}$ aryloxy, $C_{7-20}$ cycloalkyloxy, $C_{4-20}$ dienes, alkanol, alkanolamine, acetyl, acetamido, acetoacetyl, acetonyl, acetonylidene, acrylyl, alanyl, allophanoyl, anisyl, acetimido, amidino, amido, amino, aniline, anilino, arsino, azido, azino, azo, azoxy, benzamido, butryl, benzylidine, benzidyne, biphenyl), butylene, iso-butylene, sec-butylene, tert-butylene, carbonyl, carboxy, carbazoyl, caproyl, capryl, carbamido, carbamoyl, carbamyl, carbazoyl, chromyl, cinnamoyl, crotoxyl, cyanato, cyano, cyanamido, decanoly, disiloxanoxy, diazo, diazoamino, disilanyl, epoxy, ethenyl, ethynyl, formamido, formyl, furyl, furfuryl, furfurylideneyl, glutaryl, glycinamido, glycolyl, glycyl, glyocylyl, glycidyl, guanidino, guanyl, halo, hydroxyl, heptadecanoyl, heptanolyl, hydroperoxy, hydroxamino, hydroxylamido, hydrazido, heptanamido, hydrazino, hydrazo, hypophosphito, iodoso, isocyanato, isonitroso, imido, keto, lactyl, methacrylyl, malonyl, methylene, mercapto, methylenyl, nitroamino, nitro, nitrosamino, nitrosimino, nitrosylnitroso, nitrilo, naphthal, naphthobenzyl, naphthyl, naphthylidene, oxy, oxamido, peroxy, phosphinyl, phosphido, phosphito, phospho, phosphono, phosphoryl, isopropylidene, propylenyl, propylidenyl, pryidyl, pyrryl, phenethyl, phenylene, pyridino, phosphinyl, selenyl, seleninyl, selenonyl, siloxy, succinamyl, sulfamino, sulfamyl, sulfeno, silyl, silylenyl, sulfinyl, sulfo, sulfonyl, thiocarboxyl, toluoyl, thenyl, thienyl, thiobenzyl, thiocarbamyl, thiocarbonyl, thiocyanato, thionyl, thiuram, toluidino, tolyl, tolylenyl, tosyl, triazano, trihydrocarbylamino, trihaloamino, trihydrocarbyl trimethylene, trityl, tetrazinyl, ureayl, ureido, valeryl, vinylidenyl, xenyl, xylidino, xylyl, xylylenyl, and combinations thereof.

4. The polyolefin of claim 1, wherein at least one of $R^2$ and $R^3$ comprises a pyridyl functional group.

5. The polyolefin of claim 1, wherein $R^1$ comprises a $C_{2-20}$ poly-alpha-olefin having a weight average molecular weight of greater than or equal to about 2,500 g/mol.

6. The polyolefin of claim 1, wherein $R^1$ is derived from polyethylene, polypropylene, polybutadiene, butyl rubber, or a combination thereof.

7. The polyolefin of claim 1, wherein $R^1$ is derived from one or more of:
   (i) a vinyl terminated polymer having at least 5% allyl chain ends;
   (ii) a vinyl terminated polymer having an Mn of at least 200 g/mol (measured by $^1$H NMR) comprising of one or more $C_4$ to $C_{40}$ higher olefin derived units, where the higher olefin polymer comprises substantially no propylene derived units; and wherein the higher olefin polymer has at least 5% allyl chain ends;
   (iii) a copolymer having an Mn of 300 g/mol or more (measured by $^1$H NMR) comprising (a) from about 20 mol % to about 99.9 mol % of at least one $C_5$ to $C_{40}$ higher olefin, and (b) from about 0.1 mol % to about 80 mol % of propylene, wherein the higher olefin copolymer has at least 40% allyl chain ends;
   (iv) a copolymer having an Mn of 300 g/mol or more (measured by $^1$H NMR), and comprises (a) from about 80 mol % to about 99.9 mol % of at least one $C_4$ olefin, (b) from about 0.1 mol % to about 20 mol % of propylene; and wherein the vinyl terminated macromonomer has at least 40% allyl chain ends relative to total unsaturation;
   (v) a co-oligomer having an Mn of 300 g/mol to 30,000 g/mol (measured by $^1$H NMR) comprising 10 mol % to 90 mol % propylene and 10 mol % to 90 mol % of ethylene, wherein the oligomer has at least X% allyl chain ends (relative to total unsaturations), where: 1) X=(−0.94*(mol % ethylene incorporated)+100), when 10 mol % to 60 mol % ethylene is present in the co-oligomer, 2) X=45, when greater than 60 mol % and less than 70 mol % ethylene is present in the co-oligomer, and 3) X=(1.83*(mol % ethylene incorporated)−83), when 70 mol % to 90 mol % ethylene is present in the co-oligomer;
   (vi) a propylene oligomer, comprising more than 90 mol % propylene and less than 10 mol % ethylene wherein the oligomer has: at least 93% allyl chain ends, a number average molecular weight (Mn) of about 500 g/mol to about 20,000 g/mol, an isobutyl chain end to allylic vinyl group ratio of 0.8:1 to 1.35:1.0, and less than 100 ppm aluminum;
   (vii) a propylene oligomer, comprising: at least 50 mol % propylene and from 10 mol % to 50 mol % ethylene, wherein the oligomer has: at least 90% allyl chain ends, an Mn of about 150 g/mol to about 10,000 g/mol, and an isobutyl chain end to allylic vinyl group ratio of 0.8:1 to 1.2:1.0, wherein monomers having four or more carbon atoms are present at from 0 mol % to 3 mol %;
   (viii) a propylene oligomer, comprising: at least 50 mol % propylene, from 0.1 mol % to 45 mol % ethylene, and from 0.1 mol % to 5 mol % $C_4$ to $C_{12}$ olefin, wherein the oligomer has: at least 90% allyl chain ends, an Mn of about 150 g/mol to about 10,000 g/mol, and an isobutyl chain end to allylic vinyl group ratio of 0.8:1 to 1.35:1.0;
   (ix) a propylene oligomer, comprising: at least 50 mol % propylene, from 0.1 mol % to 45 mol % ethylene, and from 0.1 mol % to 5 mol % diene, wherein the oligomer has: at least 90% allyl chain ends, an Mn of about 150 g/mol to about 10,000 g/mol, and an isobutyl chain end to allylic vinyl group ratio of 0.7:1 to 1.35:1.0; and
   (x) a homo-oligomer, comprising propylene, wherein the oligomer has: at least 93% allyl chain ends, an Mn of about 500 g/mol to about 20,000 g/mol, an isobutyl chain end to allylic vinyl group ratio of 0.8:1 to 1.2:1.0, and less than 1400 ppm aluminum.

8. A polyolefin comprising one or more pyridazine moieties according to the following formulae:

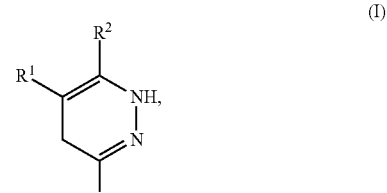
(I)

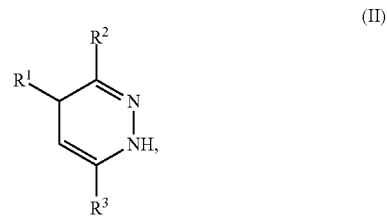
(II)

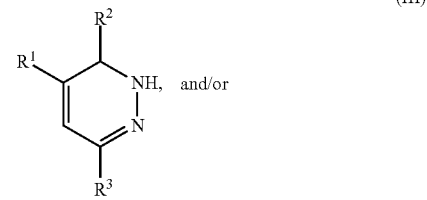
(III)

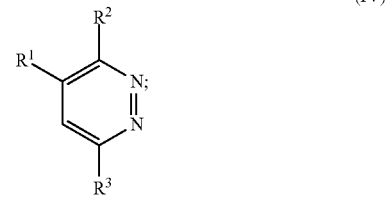
(IV)

wherein $R^1$ comprises a polyolefin chain attached to the pyridazine moiety through an aliphatic linkage, and wherein $R^2$ and $R^3$ each comprise H or one or more functional groups comprising atoms from Groups 13, 14, 15, 16, and 17 of the Periodic Table of Elements, or combinations thereof, wherein the pyridazine moiety is the cyclo-addition reaction product of a non-aromatic carbon-carbon double bond attached to a backbone of the polyolefin chain through an aliphatic linkage, and a substituted or unsubstituted tetrazine, wherein at least one of $R^2$ and $R^3$ comprises from 1 to 20 carbon atoms, nitrogen, oxygen, sulfur, phosphorous, or a combination thereof, and wherein $R^1$ is derived from polyethylene, polypropylene, polybutadiene, butyl rubber, or a combination thereof having a weight average molecular weight of greater than or equal to about 2500 g/mol.

9. The polyolefin of claim 8, wherein the non-aromatic carbon-carbon double bond is a terminal vinyl functional group.

10. The polyolefin of claim 8, wherein at least one of $R^2$ and $R^3$ comprises a pyridyl functional group.

11. The polyolefin of claim 8, wherein the tetrazine is one of 3,6-diphenyl-1,2,4,5-tetrazine, 3,6-di-2-pyridyl-1,2,4,5-tetrazine, 3,6-bis(2-chlorophenyl)-1,2,4,5-tetrazine, 3-(2-chlorophenyl)-6-(2,6-difluorophenyl)-1,2,4,5-tetrazine.

12. A composition comprising:
(a) at least one functionalized polymer comprising one or more pyridazine moieties according to the following formulae:

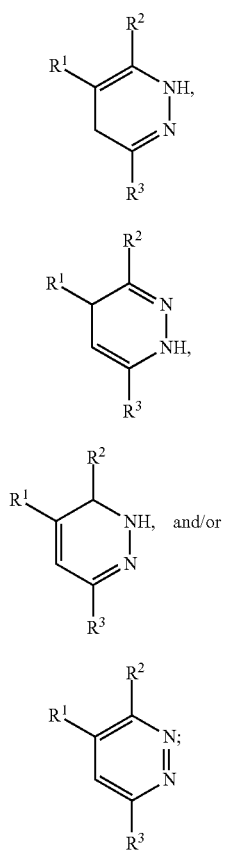

wherein $R^1$ comprises a polyolefin chain attached to the pyridazine moiety through an aliphatic linkage; and
wherein $R^2$ and $R^3$ each comprise H or one or more functional groups comprising atoms from Groups 13, 14, 15, 16, and 17 of the Periodic Table of Elements, or a combination thereof, wherein at least one of $R^2$ and $R^3$ comprises from 1 to 20 carbon atoms, nitrogen, oxygen, sulfur, phosphorous, or a combination thereof.

13. The composition of claim 12, further comprising at least one phr of a nanoclay.

14. The composition of claim 13, wherein the nanoclay is selected from montmorillonite, nontronite, beidellite, bentonite, volkonskoite, laponite, hectorite, saponite, sauconite, magadite, kenyaite, stevensite, vermiculite, halloysite, aluminate oxides, hydrotalcite, and mixtures thereof.

15. The composition of claim 12, wherein the wherein the pyridazine moiety is a terminal moiety of the polyolefin chain.

16. The composition of claim 12, wherein at least one of $R^2$ and $R^3$ comprise a functional group selected from the group consisting of:

$C_{1-20}$ linear alkyl, $C_{1-20}$ branched alkyl, $C_{1-20}$ cyclic alkyl, $C_{6-20}$ aromatic, $C_{7-20}$ alkyl-substituted aromatic, $C_{7-20}$ aryl-substituted alkyl, halogenated $C_{1-20}$ alkyl, $C_{1-20}$ alkyloxy, $C_{1-20}$ alkenyloxy, $C_{7-20}$ aryloxy, $C_{7-20}$ cycloalkyloxy, $C_{4-20}$ dienes, alkanol, alkanolamine, acetyl, acetamido, acetoacetyl, acetonyl, acetonylidene, acrylyl, alanyl, allophanoyl, anisyl, acetimido, amidino, amido, amino, aniline, anilino, arsino, azido, azino, azo, azoxy, benzamido, butryl, benzylidine, benzidyne, biphenyl), butylene, iso-butylene, sec-butylene, tert-butylene, carbonyl, carboxy, carbazoyl, caproyl, capryl, carbamido, carbamoyl, carbamyl, carbazoyl, chromyl, cinnamoyl, crotoxyl, cyanato, cyano, cyanamido, decanoly, disiloxanoxy, diazo, diazoamino, disilanyl, epoxy, ethenyl, ethynyl, formamido, formyl, furyl, furfuryl, furfurylideneyl, glutaryl, glycinamido, glycolyl, glycyl, glyocylyl, glycidyl, guanidino, guanyl, halo, hydroxyl, heptadecanoyl, heptanolyl, hydroperoxy, hydroxamino, hydroxylamido, hydrazido, heptanamido, hydrazino, hydrazo, hypophosphito, iodoso, isocyanato, isonitroso, imido, keto, lactyl, methacrylyl, malonyl, methylene, mercapto, methylenyl, nitroamino, nitro, nitrosamino, nitrosimino, nitrosylnitroso, nitrilo, naphthal, naphthobenzyl, naphthyl, naphthylidene, oxy, oxamido, peroxy, phosphinyl, phosphido, phosphito, phospho, phosphono, phosphoryl, isopropylidene, propylenyl, propylidenyl, pryidyl, pyrryl, phenethyl, phenylene, pyridino, phosphinyl, selenyl, seleninyl, selenonyl, siloxy, succinamyl, sulfamino, sulfamyl, sulfeno, silyl, silylenyl, sulfinyl, sulfo, sulfonyl, thiocarboxyl, toluoyl, thenyl, thienyl, thiobenzyl, thiocarbamyl, thiocarbonyl, thiocyanato, thionyl, thiuram, toluidino, tolyl, tolylenyl, tosyl, triazano, trihydrocarbylamino, trihaloamino, trihydrocarbyl trimethylene, trityl, tetrazinyl, ureayl, ureido, valeryl, vinylidenyl, xenyl, xylidino, xylyl, xylylenyl, and combinations thereof.

17. The composition of claim 12, wherein at least one of $R^2$ and $R^3$ comprise a pyridyl functional group.

18. The composition of claim 12, wherein $R^1$ comprises a $C_{2-20}$ poly-alpha-olefin having a weight average molecular weight of greater than or equal to about 2,500 g/mol.

19. The composition of claim 12, wherein $R^1$ is derived from polyethylene, polypropylene, polybutadiene, butyl rubber, or a combination thereof.

20. The composition of claim 12, wherein $R^1$ is derived from one or more of:
(i) a vinyl terminated polymer having at least 5% allyl chain ends;
(ii) a vinyl terminated polymer having an Mn of at least 200 g/mol (measured by $^1$H NMR) comprising of one or more $C_4$ to $C_{40}$ higher olefin derived units, where the higher olefin polymer comprises substantially no propylene derived units; and wherein the higher olefin polymer has at least 5% allyl chain ends;

(iii) a copolymer having an Mn of 300 g/mol or more (measured by $^1$H NMR) comprising (a) from about 20 mol % to about 99.9 mol % of at least one $C_5$ to $C_{40}$ higher olefin, and (b) from about 0.1 mol % to about 80 mol % of propylene, wherein the higher olefin copolymer has at least 40% allyl chain ends;

(iv) a copolymer having an Mn of 300 g/mol or more (measured by $^1$H NMR), and comprises (a) from about 80 mol % to about 99.9 mol % of at least one $C_4$ olefin, (b) from about 0.1 mol % to about 20 mol % of propylene; and wherein the vinyl terminated macromonomer has at least 40% allyl chain ends relative to total unsaturation;

(v) a co-oligomer having an Mn of 300 g/mol to 30,000 g/mol (measured by $^1$H NMR) comprising 10 mol % to 90 mol % propylene and 10 mol % to 90 mol % of ethylene, wherein the oligomer has at least X% allyl chain ends (relative to total unsaturations), where: 1) X=(−0.94*(mol % ethylene incorporated)+100), when 10 mol % to 60 mol % ethylene is present in the co-oligomer, 2) X=45, when greater than 60 mol % and less than 70 mol % ethylene is present in the co-oligomer, and 3) X=(1.83*(mol % ethylene incorporated)−83), when 70 mol % to 90 mol % ethylene is present in the co-oligomer;

(vi) a propylene oligomer, comprising more than 90 mol % propylene and less than 10 mol % ethylene wherein the oligomer has: at least 93% allyl chain ends, a number average molecular weight (Mn) of about 500 g/mol to about 20,000 g/mol, an isobutyl chain end to allylic vinyl group ratio of 0.8:1 to 1.35:1.0, and less than 100 ppm aluminum;

(vii) a propylene oligomer, comprising: at least 50 mol % propylene and from 10 mol % to 50 mol % ethylene, wherein the oligomer has: at least 90% allyl chain ends, an Mn of about 150 g/mol to about 10,000 g/mol, and an isobutyl chain end to allylic vinyl group ratio of 0.8:1 to 1.2:1.0, wherein monomers having four or more carbon atoms are present at from 0 mol % to 3 mol %;

(viii) a propylene oligomer, comprising: at least 50 mol % propylene, from 0.1 mol % to 45 mol % ethylene, and from 0.1 mol % to 5 mol % $C_4$ to $C_{12}$ olefin, wherein the oligomer has: at least 90% allyl chain ends, an Mn of about 150 g/mol to about 10,000 g/mol, and an isobutyl chain end to allylic vinyl group ratio of 0.8:1 to 1.35:1.0;

(ix) a propylene oligomer, comprising: at least 50 mol % propylene, from 0.1 mol % to 45 mol % ethylene, and from 0.1 mol % to 5 mol % diene, wherein the oligomer has: at least 90% allyl chain ends, an Mn of about 150 g/mol to about 10,000 g/mol, and an isobutyl chain end to allylic vinyl group ratio of 0.7:1 to 1.35:1.0; and (x) a homo-oligomer, comprising propylene, wherein the oligomer has: at least 93% allyl chain ends, an Mn of about 500 g/mol to about 20,000 g/mol, an isobutyl chain end to allylic vinyl group ratio of 0.8:1 to 1.2:1.0, and less than 1400 ppm aluminum.

21. The composition of claim 12, further comprising one or more of fillers, antioxidants, oils, or adhesion promoters.

22. A nanocomposite, coating, anti-fouling coating, metal composite, metal complex, disinfectant, wetting agent, dispersant, viscosity index or multifunctional viscosity index additive comprising the composition of claim 12.

* * * * *